United States Patent [19]

Ohba et al.

[11] Patent Number: 5,076,834
[45] Date of Patent: Dec. 31, 1991

[54] 1,2,5,6-TETRAHYDROPYRIDINE-2-ONE COMPOUNDS WHICH ARE USEFUL HERBICIDES

[75] Inventors: Nobuyuki Ohba, Iwata; Atsuhiko Ikeda, Shizuoka; Kenji Matsunari, Fujieda; Yuji Yamada; Michiya Hirata, both of Shizuoka; Yasuo Nakamura, Tokyo; Akira Takeuchi, Kakegawa; Hiroyuki Karino, Shizuoka, all of Japan

[73] Assignees: Kumiai Chemical Industry Co., Ltd.; Ihara Chemical Industry Co., Ltd., both of Tokyo, Japan

[21] Appl. No.: 593,755

[22] Filed: Oct. 5, 1990

Related U.S. Application Data

[62] Division of Ser. No. 442,735, Nov. 28, 1989, Pat. No. 5,006,157.

[30] Foreign Application Priority Data

Dec. 9, 1988 [JP] Japan .................. 63-311635
Oct. 12, 1989 [JP] Japan .................. 63-265900

[51] Int. Cl.$^5$ .......................................... C07D 211/68
[52] U.S. Cl. ............................. 71/94; 546/290; 546/300; 546/301; 546/302; 546/303
[58] Field of Search ............... 546/290, 300, 301, 302, 546/303; 71/94

[56] References Cited

U.S. PATENT DOCUMENTS 3,272,842 9/1966 Easton et al. .................. 548/290

FOREIGN PATENT DOCUMENTS 2735841 2/1978 Fed. Rep. of Germany ...... 548/290
2050806 4/1981 United Kingdom ............. 546/290

OTHER PUBLICATIONS

Chemical Abstracts, vol. 60, No. 5, Abstract 7986a, Hohenlohe-Oehringen et al., Mar. 2, 1964.

*Primary Examiner*—C. Warren Ivy
*Assistant Examiner*—Zinna Northington-Davis
*Attorney, Agent, or Firm*—Oblon, Spivak, McClelland, Maier & Neustadt

[57] ABSTRACT

A cyclic amide compound of the formula:

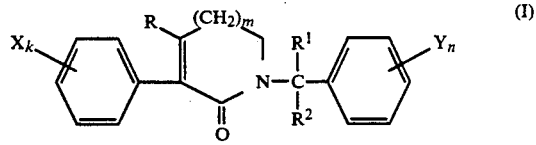

wherein X is a hydrogen atom, a halogen atom, a lower alkyl group, a haloalkyl group, a lower alkoxy group, a haloalkoxy group, a lower alkylthio group or a nitro group; Y is a hydrogen atom, a halogen atom, an alkykl roup, a cycloalkyl group, an alkenyl group, an alkylnyl group, a haloalkyl group, a phenyl group, an alkoxy group, a cycloalkoxy group, a cycloalkylalkoxy group, an alkenyloxy group, an alkynloxy group, a benzyloxy group, a phenoxy group, a haloalkoxy group, a lower alkoxy-lower alkoxy group, a cyanoalkoxy group, an alkylthio group, an alkenylthio group, an alkynylthio group, a benzylthio group, a phenylthio group,

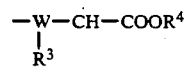

(wherein W is an oxygen atom or a sulfuratom, $R^3$ is a hydrogen atom or an alkyl group and $R^4$ is an alkyl group),

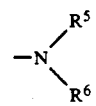

(wherein each of $R^5$ and $R^6$ is a hydrogen atom or a lower alkyl group), an alkylsulfonyl group,

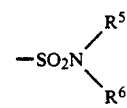

(wherein $R^5$ and $R^6$ are as defined above an alkylcarbonyl group, an alkoxy carbonyl group, a hydroxy carbonyl group, a nitro group, a cyano group or a hydroxyl group; R is a hydrogen same or different is an alkyl group, or $R^1$ and $R^2$ together with the adjacent carbon atom form a ring; m is 0 or 1; n is an integer of from 1 to 5; and k is an integer of 1 or 2.

18 Claims, No Drawings

1,2,5,6-TETRAHYDROPYRIDINE-2-ONE COMPOUNDS WHICH ARE USEFUL HERBICIDES

This is a division of application Ser. No. 07/442,735, filed on Nov. 28, 1989 now U.S. Pat. No. 5,006,157.

The present invention relates to novel cyclic amide compounds. More particularly, the present invention relates to novel cyclic amide compounds of the formula I as shown hereinafter, and herbicidal compositions containing them. Therefore, the present invention is useful in the chemical industry and agriculture, particularly in the manufacture of agricultural chemicals.

Heretofore, some cyclic amide compounds having herbicidal activities have been known. For example, Japanese Unexamined Paten Publication No. 70283/1979 discloses that a compound of the formula:

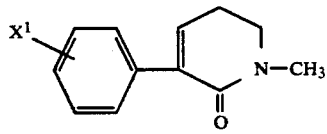

wherein $X^1$ is a hydrogen atom, a lower alkyl group, a lower alkoxy group or a halogen atom, exhibits herbicidal activities. Further, U.S. Pat. No. 3,272,842 discloses a compound of the formula:

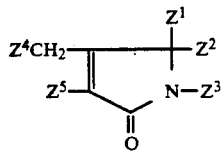

wherein each of $Z^1$ and $Z^2$ is a lower alkyl group or an unsubstituted or substituted phenyl group, $Z^3$ is a hydrogen atom, a lower alkyl group, a cycloalkyl group, an alkoxyalkyl group or a tetrahydrofurfuryl group, $Z^4$ is a hydrogen atom, a lower alkyl group, a phenyl group or a naphthyl group, and $Z^5$ is an unsubstituted or substituted phenyl group, a phenoxy group, a phenylthio group, a naphthyl group, a naphthyloxy group, a naphthylthio group or a thienyl group, as a selective herbicide useful for soil treatment and foliage treatment.

Further, Belgian Patent No. 857,684 discloses a compound of the formula:

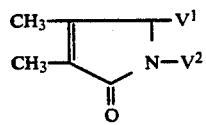

wherein $V^1$ is a hydroxyl group, a halogen atom or an acyloxy group, and $V^2$ is an aryl group, an aralkyl group or a hetero ring, as a selective herbicide.

Known cyclic amide compounds have a certain level of herbicidal activities and selectivities. However, the herbicidal activities and selectivities are not always adequate.

In recent years, it is strongly desired to develop a herbicide having a selectivity for killing weeds without adversely affecting crop plants even if it is applied to crop plants and weeds at the same time. Further, it is desired to develop an effective herbicide which can certainly control weeds which are usually hardly controlable in upland fields or paddy fields such as purple nutsedge (*Cyperus rotundus*), cyperus (*Cyperus serotinus*) and bulrush (*Scirpus juncoides*). Further, it is desired to develop a herbicide which exhibits high herbicidal effects at a low dose, and, the same time, does not remain in the environment over a long period of time and does not polute ground water and rivers.

It is the object of the present invention to provide a herbicide satisfying the above-mentioned requirements, and to solve the problems in the field of herbicides.

The present invention provides novel cyclic amide compounds which are practically highly useful as herbicides in place of known cyclic amide compounds.

The present inventors have synthesized many cyclic amide compounds in order to attain the above-mentioned object, and have conducted extensive researches on the usefulness of those compounds. As the results, they have succeeded in the synthesis of cyclic amide compounds having a substituted α,α-dialkyl-benzyl group. They have found that these compounds are novel compounds which have not been disclosed in any literatures, and that these compounds exhibit higher herbicidal activities and selectivity than known cyclic amide compounds. The present invention has been accomplished on the basis of these discoveries.

The present invention provides a cyclic amide compound of the formula:

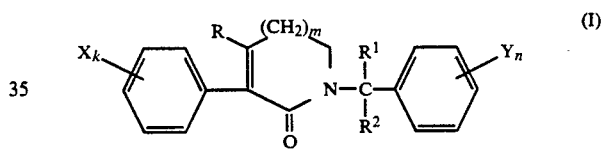

wherein X is a hydrogen atom, a halogen atom, a lower alkyl group, preferably a $C_1$–$C_4$ alkyl group, a haloalkyl group, a preferably a $C_1$–$C_4$ haloalkyl group, a lower alkoxy group, preferably a $C_1$–$C_4$ alkoxy group, a haloalkoxy group, preferably a $C_1$–$C_4$ haloalkoxy group, a lower alkylthio group, preferably a $C_1$–$C_4$ alkylthio group, or a nitro group; Y is a hydrogen atom, a halogen atom, an alkyl group, preferably a $C_1$–$C_8$ alkyl group, a cycloalkyl group, a $C_3$–$C_6$ cycloalkyl group, an alkenyl group, preferably a $C_2$–$C_8$ alkenyl group, an alkynyl group, preferably a $C_2$–$C_8$ alkynyl group, a haloalkyl group, preferably a $C_1$–$C_8$ haloalkyl group, a phenyl group, an alkoxy group, preferably a $C_1$–$C_8$ alkoxy group, a cycloalkoxy group, preferably a $C_3$–$C_6$ cycloalkoxy group, a cycloalkyl alkoxy group, preferably a $C_3$–$C_6$ cycloalkyl, a $C_1$–$C_4$ alkoxy group, an alkenyloxy group, preferably a $C_3$–$C_8$ alkenyloxy group, an alkynyloxy group, preferably a $C_3$–$C_8$ alkynyloxy group, a benzyloxy group, a phenoxy group, a haloalkoxy group, preferably a $C_1$–$C_8$ haloalkoxy group, a lower alkoxy-lower alkoxy group, preferably a $C_1$–$C_4$ alkoxy-$C_1$–$C_4$ alkoxy group, a cyanoalkoxy group, preferably a $C_1$–$C_4$ cyanoalkoxy group, an alkylthio group, preferably a $C_1$–$C_8$ alkylthio group, a haloalkylthio group, preferably a $C_1$–$C_8$ haloalkylthio group, an alkenylthio group, preferably a $C_3$–$C_8$ alkenylthio group, an alkynylthio group, preferably a $C_3$–$C_8$ alkynylthio group, a benzylthio group, a phenylthio group,

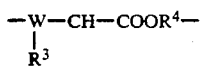

(wherein W is an oxygen atom or a sulfur atom, $R^3$ is a hydrogen atom or alkyl group, preferably a $C_1$-$C_4$ alkyl group, and $R^4$ is an alkyl group, preferably a $C_1$-$C_8$ alkyl group),

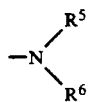

(wherein each of $R^5$ and $R^6$ is a hydrogen atom or a lower alkyl group, preferably a $C_1$-$C_4$ alkyl group), an alkyl sulfonyl group, a

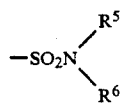

(wherein $R^5$ and $R^6$ are as defined above), an alkyl carbonyl group, preferably a $C_1$-$C_4$ alkyl carbonyl group, an alkoxy carbonyl group, preferably a $C_1$-$C_4$ alkoxy carbonyl group, a hydroxy carbonyl group, a nitro group, a cyano group or a hydroxy group; R is a hydrogen atom or a lower alkyl group, preferably a $C_1$-$C_4$ alkyl group; each of $R^1$ and $R^2$ which may be the same or different is an alkyl group, preferably a $C_1$-$C_4$ alkyl group, or $R^1$ and $R^2$ together with the adjacent carbon atom form a ring; m is zero or 1; n is an integer of from 1 to 5; and k is an integer of 1 or 2.

The present invention also provides a herbicidal composition comprising a herbicidally effective amount of a cyclic amide compound of the formula I as defined above as an active ingredient, and an agricultural ajuvant.

Further, the present invention provides a method for killing weeds which comprises applying a herbicidally effective amount of a cyclic amide compound of the formula I as defined above to a locus to be protected.

Now, the present invention will be described in detail with reference to the preferred embodiments.

In the formula I, X is preferably a hydrogen atom, a halogen atom, a lower alkyl group, a haloalkyl group or a lower alkoxy group, more preferably a hydrogen atom or a halogen atom.

Y is preferably a hydrogen atom, a halogen atom, a lower alkyl group, a haloalkyl group, a lower alkoxy group, a phenoxy group or a haloalkoxy group, more preferably a hydrogen atom, a halogen atom, a lower alkyl group, a haloalkyl group, a lower alkoxy group or a phenoxy group.

R is preferably a hydrogen atom, a methyl group or an ethyl group, more preferably a methyl group.

Each of $R^1$ and $R^2$ is preferably a methyl group.

m is preferably 0.

When n is an integer of from 2 to 5, the plurality of Y are preferably different from one another.

When n is 1, Y is preferably a halogen atom substituted at o-position.

When n is an integer of 1, 2 or 3, Y is preferably a hydrogen atom or a halogen atom.

When n is 3, two or three Y are halogen atoms.

Further, the preferred compound is a compound wherein in the formula I, X is a hydrogen atom or a halogen atom, Y is a hydrogen atom, a halogen atom, a lower alkyl group, alkoxy group, a haloalkyl group, a lower alkoxy group, a phenoxy group, R is a methyl group, each of $R^1$ and $R^2$ is a methyl group, and m is 0.

Now, typical examples of the compound of the formula I of the present invention will be presented in Table 1. Compound Nos. given in the Table will be referred to in the subsequent description in the specification.

TABLE 1

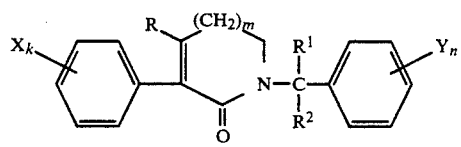

| Compound No. | Xk | R | $R^1$ | $R^2$ | Yn | m | Melting point (°C.) or refractive index ($n_D^{20}$) |
|---|---|---|---|---|---|---|---|
| 1 | H | H | $CH_3$ | $CH_3$ | H | 1 | 119-120 |
| 2 | H | H | $CH_3$ | $CH_3$ | 2-Cl | 1 | 104-106 |
| 3 | H | H | $CH_3$ | $CH_3$ | 3-Cl | 1 | 135-137 |
| 4 | H | H | $CH_3$ | $CH_3$ | 4-Cl | 1 | 135-137 |
| 5 | H | H | $CH_3$ | $CH_3$ | 3-F | 1 | 76-78 |
| 6 | H | H | $CH_3$ | $CH_3$ | 3,4-$Cl_2$ | 1 | 132-134 |
| 7 | H | $CH_3$ | $CH_3$ | $CH_3$ | H | 1 | 108-109 |
| 8 | H | $CH_3$ | $CH_3$ | $CH_3$ | 2-Cl | 1 | 1.5931 |
| 9 | H | $CH_3$ | $CH_3$ | $CH_3$ | 3-Cl | 1 | 117-118 |
| 10 | H | $CH_3$ | $CH_3$ | $CH_3$ | 4-Cl | 1 | 133-135 |
| 11 | H | $CH_3$ | $CH_3$ | $CH_3$ | 3-F | 1 | 103-105 |
| 12 | H | $CH_3$ | $CH_3$ | $CH_3$ | 4-F | 1 | 122-125 |
| 13 | H | $CH_3$ | $CH_3$ | $CH_3$ | 3,4-$Cl_2$ | 1 | 124-126 |
| 14 | H | $CH_3$ | $CH_3$ | $CH_3$ | 3,5-$Cl_2$ | 1 | 145-147 |
| 15 | H | $CH_3$ | $CH_3$ | $CH_3$ | 3,4-$F_2$ | 1 | 89-91 |
| 16 | H | $CH_3$ | $CH_3$ | $CH_3$ | 2-F | 1 | 107-109 |
| 17 | H | $CH_3$ | $CH_3$ | $CH_3$ | 2-$CH_3$ | 1 | 105-108 |
| 18 | H | $CH_3$ | $CH_3$ | $CH_3$ | 3-$OCH_3$ | 1 | 72-74 |
| 19 | H | $CH_3$ | $CH_3$ | $CH_3$ | 4-$OCH_3$ | 1 | 95-97 |
| 20 | H | $CH_3$ | $CH_3$ | $CH_3$ | 3-$CH_3$ | 1 | 75-77 |
| 21 | H | $C_2H_5$ | $CH_3$ | $CH_3$ | H | 1 | 74-76 |

TABLE 1-continued

| Compound No. | $X_k$ | R | $R^1$ | $R^2$ | $Y_n$ | m | Melting point (°C.) or refractive index ($n_D^{20}$) |
|---|---|---|---|---|---|---|---|
| 22 | 2-Cl | H | CH₃ | CH₃ | H | 1 | 106–107 |
| 23 | 2-Cl | H | CH₃ | CH₃ | 3-Cl | 1 | 99–100 |
| 24 | 2-Cl | CH₃ | CH₃ | CH₃ | H | 1 | 112–114 |
| 25 | 2-Cl | CH₃ | CH₃ | CH₃ | 3-Cl | 1 | 120–122 |
| 26 | 2-Cl | CH₃ | CH₃ | CH₃ | 3-F | 1 | 127–129 |
| 27 | 3-Cl | H | CH₃ | CH₃ | H | 1 | 82–83 |
| 28 | 3-Cl | CH₃ | CH₃ | CH₃ | H | 1 | 1.5923 |
| 29 | 3-Cl | CH₃ | CH₃ | CH₃ | 3-Cl | 1 | 113–116 |
| 30 | 3-Cl | CH₃ | CH₃ | CH₃ | 3-F | 1 | 69–72 |
| 31 | 4-Cl | H | CH₃ | CH₃ | H | 1 | 123–125 |
| 32 | 4-Cl | CH₃ | CH₃ | CH₃ | H | 1 | 125–127 |
| 33 | 4-Cl | CH₃ | CH₃ | CH₃ | 3-Cl | 1 | 82–85 |
| 34 | 4-Cl | CH₃ | CH₃ | CH₃ | 3-F | 1 | 115–118 |
| 35 | 2-F | H | CH₃ | CH₃ | H | 1 | 118–120 |
| 36 | 2-F | H | CH₃ | CH₃ | 3-Cl | 1 | 122–124 |
| 37 | 2-F | H | CH₃ | CH₃ | 3-F | 1 | 84–86 |
| 38 | 2-F | CH₃ | CH₃ | CH₃ | H | 1 | 88–90 |
| 39 | 2-F | CH₃ | CH₃ | CH₃ | 3-Cl | 1 | 97–98 |
| 40 | 2-F | CH₃ | CH₃ | CH₃ | 3-F | 1 | 101–103 |
| 41 | 3-F | CH₃ | CH₃ | CH₃ | H | 1 | 81–82 |
| 42 | 3-F | CH₃ | CH₃ | CH₃ | 3-Cl | 1 | 120–122 |
| 43 | 3-F | CH₃ | CH₃ | CH₃ | 3-F | 1 | 97–99 |
| 44 | 4-F | CH₃ | CH₃ | CH₃ | H | 1 | 93–95 |
| 45 | 4-F | CH₃ | CH₃ | CH₃ | 3-Cl | 1 | 112–113 |
| 46 | 4-F | CH₃ | CH₃ | CH₃ | 3-F | 1 | 90–92 |
| 47 | 2-CF₃ | H | CH₃ | CH₃ | H | 1 | 77–80 |
| 48 | 2-CF₃ | CH₃ | CH₃ | CH₃ | H | 1 | 1.5405 |
| 49 | 3-CF₃ | CH₃ | CH₃ | CH₃ | H | 1 | 68–69 |
| 50 | 3-CF₃ | CH₃ | CH₃ | CH₃ | 3-Cl | 1 | 1.5441 |
| 51 | 3-CF₃ | CH₃ | CH₃ | CH₃ | 3-F | 1 | 1.5365 |
| 52 | 2-CF₃ | CH₃ | CH₃ | CH₃ | 3-Cl | 1 | 101–103 |
| 53 | 2-CF₃ | CH₃ | CH₃ | CH₃ | 3-F | 1 | 95–97 |
| 54 | 2-CH₃ | H | CH₃ | CH₃ | H | 1 | 81–84 |
| 55 | 2-CH₃ | H | CH₃ | CH₃ | 3-Cl | 1 | 71–73 |
| 56 | 2-CH₃ | CH₃ | CH₃ | CH₃ | H | 1 | 103–104 |
| 57 | 2-CH₃ | CH₃ | CH₃ | CH₃ | 3-Cl | 1 | 93–96 |
| 58 | 2-CH₃ | CH₃ | CH₃ | CH₃ | 3-F | 1 | 114–116 |
| 59 | 3-CH₃ | CH₃ | CH₃ | CH₃ | H | 1 | 1.5767 |
| 60 | 3-CH₃ | CH₃ | CH₃ | CH₃ | 3-Cl | 1 | 1.5862 |
| 61 | 3-CH₃ | CH₃ | CH₃ | CH₃ | 3-F | 1 | 96–98 |
| 62 | 4-CH₃ | CH₃ | CH₃ | CH₃ | H | 1 | 97–98 |
| 63 | 4-CH₃ | CH₃ | CH₃ | CH₃ | 3-Cl | 1 | 79–80 |
| 64 | 4-CH₃ | CH₃ | CH₃ | CH₃ | 3-F | 1 | 86–88 |
| 65 | 2-OCH₃ | H | CH₃ | CH₃ | H | 1 | 53–55 |
| 66 | 2-OCH₃ | CH₃ | CH₃ | CH₃ | H | 1 | 80–82 |
| 67 | 2-OCH₃ | CH₃ | CH₃ | CH₃ | 3-Cl | 1 | 123–125 |
| 68 | 2-OCH₃ | CH₃ | CH₃ | CH₃ | 3-F | 1 | 110–112 |
| 69 | 3-OCH₃ | CH₃ | CH₃ | CH₃ | H | 1 | 1.5889 |
| 70 | 3-OCH₃ | CH₃ | CH₃ | CH₃ | 3-Cl | 1 | 93–94 |
| 71 | 3-OCH₃ | CH₃ | CH₃ | CH₃ | 3-F | 1 | 71–73 |
| 72 | 4-OCH₃ | CH₃ | CH₃ | CH₃ | H | 1 | 97–100 |
| 73 | 4-OCH₃ | CH₃ | CH₃ | CH₃ | 3-Cl | 1 | 109–112 |
| 74 | 4-OCH₃ | CH₃ | CH₃ | CH₃ | 3-F | 1 | 90–92 |
| 75 | H | CH₃ | CH₃ | CH₃ | 3-OCHF₂ | 1 | 68–69 |
| 76 | H | CH₃ | CH₃ | CH₃ | 3,4,5-Cl₃ | 1 | 160–163 |
| 77 | H | CH₃ | C₂H₅ | CH₃ | H | 1 | 1.5736 |
| 78 | H | CH₃ | CH₃ | CH₃ | 3-CF₃ | 1 | 101–103 |
| 79 | H | CH₃ | CH₃ | CH₃ | 3,5-(CH₃)₂ | 1 | 94–95 |
| 80 | H | CH₃ | CH₃ | C₂H₅ | 3-Cl | 1 | 96–98 |
| 81 | H | CH₃ | —(CH₂)₂— | | 3-Cl | 1 | 120–121 |
| 82 | H | CH₃ | CH₃ | CH₃ | 4-Br | 1 | 162–163 |
| 83 | H | CH₃ | —(CH₂)₂— | | 3,5-Cl₂ | 1 | 109–110 |
| 84 | H | CH₃ | CH₃ | CH₃ | 3,5-Cl₂ 4-F | 1 | 154–159 |
| 85 | H | CH₃ | CH₃ | CH₃ | H | 0 | 75–77 |
| 86 | H | CH₃ | CH₃ | CH₃ | 3-F | 0 | 91–93 |
| 87 | H | CH₃ | CH₃ | CH₃ | 2-Cl | 0 | 131–133 |
| 88 | H | CH₃ | CH₃ | CH₃ | 3-Cl | 0 | 102–103 |
| 89 | H | CH₃ | CH₃ | CH₃ | 4-Cl | 0 | 79–81 |
| 90 | H | CH₃ | CH₃ | CH₃ | 2-CH₃ | 0 | 153–155 |
| 91 | H | CH₃ | CH₃ | CH₃ | 3-CH₃ | 0 | 123–125 |

TABLE 1-continued

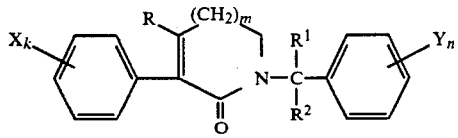

| Compound No. | Xk | R | R¹ | R² | Yn | m | Melting point (°C.) or refractive index ($n_D^{20}$) |
|---|---|---|---|---|---|---|---|
| 92 | H | $CH_3$ | $CH_3$ | $CH_3$ | 3-$OCH_3$ | 0 | 70–71 |
| 93 | H | $CH_3$ | $CH_3$ | $CH_3$ | 3,4-$Cl_2$ | 0 | 1.5992 |
| 94 | H | $CH_3$ | $CH_3$ | $CH_3$ | 3,5-$Cl_2$ | 0 | 150–152 |
| 95 | H | $C_2H_5$ | $CH_3$ | $CH_3$ | 3-Cl | 0 | 121–122 |
| 96 | 2-Cl | $CH_3$ | $CH_3$ | $CH_3$ | H | 0 | 138–140 |
| 97 | 2-Cl | $CH_3$ | $CH_3$ | $CH_3$ | 3-Cl | 0 | 84–86 |
| 98 | 3-Cl | $CH_3$ | $CH_3$ | $CH_3$ | H | 0 | 65–67 |
| 99 | 3-Cl | $CH_3$ | $CH_3$ | $CH_3$ | 3-Cl | 0 | 91–93 |
| 100 | 4-Cl | $CH_3$ | $CH_3$ | $CH_3$ | H | 0 | 115–117 |
| 101 | 4-Cl | $CH_3$ | $CH_3$ | $CH_3$ | 3-Cl | 0 | Not measurable |
| 102 | 2-F | $CH_3$ | $CH_3$ | $CH_3$ | H | 0 | 114–115 |
| 103 | 2-F | $CH_3$ | $CH_3$ | $CH_3$ | 3-Cl | 0 | 82–83 |
| 104 | 2-F | $CH_3$ | $CH_3$ | $CH_3$ | 4-Cl | 0 | 90–91 |
| 105 | 3-F | $CH_3$ | $CH_3$ | $CH_3$ | H | 0 | 60–61 |
| 106 | 3-F | $CH_3$ | $CH_3$ | $CH_3$ | 3-Cl | 0 | 70–72 |
| 107 | 2-$CH_3$ | $CH_3$ | $CH_3$ | $CH_3$ | H | 0 | 113–116 |
| 108 | 2-$OCH_3$ | $CH_3$ | $CH_3$ | $CH_3$ | H | 0 | 1.5880 |
| 109 | 2-$CF_3$ | $CH_3$ | $CH_3$ | $CH_3$ | H | 0 | 107–109 |
| 110 | H | $CH_3$ | $CH_3$ | $CH_3$ | 2,4-$F_2$ | 0 | 134–137 |
| 111 | H | $CH_3$ | $CH_3$ | $CH_3$ | 3,5-$Cl_2$ 3,5-$Br_2$ | 0 | 160–165 |
| 112 | 2-F | $CH_3$ | $CH_3$ | $CH_3$ | 3,4,5-$Cl_3$ | 0 | 191–197 |
| 113 | H | $CH_3$ | $CH_3$ | $CH_3$ | 3,4,5-$Cl_3$ | 0 | 181–183 |
| 114 | H | $CH_3$ | $CH_3$ | $CH_3$ | 3,5-$Cl_2$ 4-F | 0 | 164–167 |
| 115 | H | $CH_3$ | $CH_3$ | $CH_3$ | 3-Br | 0 | 86–88 |
| 116 | H | $CH_3$ | $CH_3$ | $CH_3$ | 3,4-$F_2$ | 0 | 104–106 |
| 117 | H | $CH_3$ | $CH_3$ | $CH_3$ | 3-$CF_3$ | 0 | 77–78 |
| 118 | H | $CH_3$ | $CH_3$ | $CH_3$ | 3,5-$(CH_3)_2$ | 0 | 86–89 |
| 119 | H | $CH_3$ | $CH_3$ | $CH_3$ | 3-$OCHF_2$ | 0 | 68–70 |
| 120 | H | $CH_3$ | $CH_3$ | $CH_3$ | 3-$OC_2H_5$ | 0 | 1.5805 |
| 121 | H | $CH_3$ | —$(CH_2)_2$— | | H | 0 | 136–137 |
| 122 | H | $CH_3$ | $CH_3$ | $CH_3$ | 3-$OC_3H_7$-i | 0 | 99–100 |
| 123 | H | $CH_3$ | $CH_3$ | $CH_3$ | 3-$OC_3H_7$ | 0 | 1.5749 |
| 124 | H | $CH_3$ | $CH_3$ | $C_3H_7$-i | H | 0 | 103–105 |
| 125 | H | $CH_3$ | $CH_3$ | $CH_3$ | 4-F | 0 | 125–126 |
| 126 | H | H | $CH_3$ | $CH_3$ | H | 0 | 85–86 |
| 127 | H | H | $CH_3$ | $CH_3$ | 3-Cl | 0 | 95–96 |
| 128 | H | $CH_3$ | $C_2H_5$ | $CH_3$ | 3-Cl | 0 | 105–107 |
| 129 | H | $CH_3$ | —$(CH_2)_2$— | | 3-Cl | 0 | 152–153 |
| 130 | H | $CH_3$ | $CH_3$ | $CH_3$ | 4-Br | 0 | 93–94 |
| 131 | H | $CH_3$ | $CH_3$ | $CH_3$ | 2-F | 0 | 110–113 |
| 132 | H | $CH_3$ | $CH_3$ | $CH_3$ | 2,4-$Cl_2$ | 0 | 144–148 |
| 133 | H | $CH_3$ | —$(CH_2)_2$— | | 3,5-$Cl_2$ | 0 | 145–146 |
| 134 | 2-F | $CH_3$ | $CH_3$ | $CH_3$ | 3,5-$Cl_2$ | 0 | 177–180 |
| 135 | 2-Cl | $CH_3$ | $CH_3$ | $CH_3$ | 3,5-$Cl_2$ | 0 | 145–148 |
| 136 | H | H | $CH_3$ | $CH_3$ | 3,5-$Cl_2$ | 0 | 181–187 |
| 137 | H | $CH_3$ | $CH_3$ | $CH_3$ | 3,5-$(OCH_3)_2$ | 0 | 112–115 |
| 138 | H | $CH_3$ | $CH_3$ | $CH_3$ | 4-$CF_3$ | 0 | 87–92 |
| 139 | H | $CH_3$ | $CH_3$ | $CH_3$ | 3-I | 0 | 81–85 |
| 140 | H | $CH_3$ | $CH_3$ | $CH_3$ | 4-$OCH_3$ | 0 | Not measurable |
| 141 | 2-F | $CH_3$ | $CH_3$ | $CH_3$ | 3,5-$Cl_2$ 4-F | 0 | 200–205 |
| 142 | 2-Cl | $CH_3$ | $CH_3$ | $CH_3$ | 3,5-$Cl_2$ 4-F | 0 | 168–172 |
| 143 | H | $CH_3$ | $CH_3$ | $CH_3$ | 3,5-$Cl_2$ 4-$OCH_3$ | 0 | 136–139 |
| 144 | 2-Cl | $CH_3$ | $CH_3$ | $CH_3$ | 3,4,5-$Cl_3$ | 0 | 160–170 |
| 145 | 2-Cl | $CH_3$ | $CH_3$ | $CH_3$ | 3,4-$F_2$ | 0 | 126–130 |
| 146 | H | $CH_3$ | $CH_3$ | $CH_3$ | 3,5-$(CF_3)_2$ | 0 | 125–127 |
| 147 | 2-Cl | $CH_3$ | $CH_3$ | $CH_3$ | 3-F | 0 | 86–90 |
| 148 | H | $CH_3$ | $CH_3$ | $CH_3$ | 2,3,4,5,6-$F_5$ | 0 | 105–107 |
| 149 | H | $CH_3$ | $CH_3$ | $CH_3$ | 3,5-$Cl_2$ 4-$OCH_3H_7$-i | 0 | 148–150 |
| 150 | H | $CH_3$ | $CH_3$ | $CH_3$ | 2,6-$F_2$ | 0 | 120–122 |
| 151 | H | $CH_3$ | $CH_3$ | $CH_3$ | 2,5-$Cl_2$ | 0 | 196–199 |
| 152 | H | $CH_3$ | $CH_3$ | $CH_3$ | 2,3-$Cl_2$ | 0 | 152–155 |
| 153 | H | $CH_3$ | $CH_3$ | $CH_3$ | 3,5-$I_2$ | 0 | 137–138 |
| 154 | 2-F | $CH_3$ | $CH_3$ | $CH_3$ | 3-$CF_3$ | 0 | 1.5470 |
| 155 | 2-Cl | $CH_3$ | $CH_3$ | $CH_3$ | 3,4-$Cl_2$ | 0 | Not measurable |
| 156 | 2-F | $CH_3$ | $CH_3$ | $CH_3$ | 3,4-$Cl_2$ | 0 | Not measurable |

TABLE 1-continued $$X_k \underset{}{\overset{R}{\bigcirc}} \overset{(CH_2)_m}{\underset{\overset{\parallel}{O}}{C}} N - \underset{R^2}{\overset{R^1}{C}} \bigcirc Y_n$$

| Compound No. | Xk | R | R¹ | R² | Yn | m | Melting point (°C.) or refractive index ($n_D^{20}$) |
|---|---|---|---|---|---|---|---|
| 157 | H | CH₃ | CH₃ | CH₃ | 3-Cl, 4-F | 0 | 110–112 |
| 158 | 2-F | CH₃ | CH₃ | CH₃ | 3-Cl, 4-F | 0 | 126–128 |
| 159 | 2-Cl | CH₃ | CH₃ | CH₃ | 3-Cl, 4-F | 0 | 104–107 |
| 160 | H | CH₃ | CH₃ | CH₃ | 3,5-(OCHF₂)₂ | 0 | 94–96 |
| 161 | H | CH₃ | CH₃ | CH₃ | 3,5-Cl₂ 4-OCHF₂ | 0 | 125–127 |
| 162 | 2-F | CH₃ | CH₃ | CH₃ | 3,5-Cl₂ 4-OCHF₂ | 0 | 130–134 |
| 163 | H | CH₃ | CH₃ | CH₃ | 3,5-F₂ | 0 | 126–128 |
| 164 | 2-Cl | CH₃ | CH₃ | CH₃ | 3,5-F₂ | 0 | 116–120 |
| 165 | 2-F | CH₃ | CH₃ | CH₃ | 3,5-Cl₂ 4-OCH₃ | 0 | 145–147 |
| 166 | 2-F | CH₃ | CH₃ | CH₃ | 3-F | 0 | 114–117 |
| 167 | 2-F | H | CH₃ | CH₃ | 3,5-Cl₂ | 1 | |
| 168 | H | H | CH₃ | CH₃ | 3,5-Cl₂, 4-OCH₃ | 1 | |
| 169 | 2-OCHF₂ | CH₃ | CH₃ | CH₃ | 3-F | 1 | |
| 170 | 2,6-Cl₂ | CH₃ | CH₃ | CH₃ | 3-F | 1 | |
| 171 | 2-CH₃ | CH₃ | CH₃ | CH₃ | 3-Cl | 1 | |
| 172 | 2-CF₃ | CH₃ | CH₃ | CH₃ | 3-Cl | 1 | |
| 173 | 2,6-F₂ | CH₃ | CH₃ | CH₃ | 3-Cl | 1 | |
| 174 | 2,6-Cl₂ | CH₃ | CH₃ | CH₃ | 3-Cl | 1 | |
| 175 | 2-F | CH₃ | CH₃ | CH₃ | 3-Br | 1 | |
| 176 | 2-F | CH₃ | CH₃ | CH₃ | 3-I | 1 | |
| 177 | 2-Cl | CH₃ | CH₃ | CH₃ | 3-CH₃ | 1 | |
| 178 | H | CH₃ | CH₃ | CH₃ | 3-C₂H₅ | 1 | |
| 179 | H | CH₃ | CH₃ | CH₃ | 4-C₂H₅ | 1 | |
| 180 | H | CH₃ | CH₃ | CH₃ | 4-C₃H₇-n | 1 | |
| 181 | H | CH₃ | CH₃ | CH₃ | 4-C₃H₇-i | 1 | |
| 182 | H | CH₃ | CH₃ | CH₃ | 4-C₄H₉-n | 1 | |
| 183 | H | CH₃ | CH₃ | CH₃ | 4-C₄H₉-t | 1 | |
| 184 | H | CH₃ | CH₃ | CH₃ | 4-C₅H₁₁-n | 1 | |
| 185 | H | CH₃ | CH₃ | CH₃ | 4-(cyclohexyl-H) | 1 | |
| 186 | H | CH₃ | CH₃ | CH₃ | 3-C(CH₃)=CH₂ | 1 | |
| 187 | H | CH₃ | CH₃ | CH₃ | 4-CH=CH₂ | 1 | |
| 188 | H | CH₃ | CH₃ | CH₃ | 4-C(CH₃)=CH₂ | 1 | |
| 189 | H | CH₃ | CH₃ | CH₃ | 3-C≡CH | 1 | |
| 190 | H | CH₃ | CH₃ | CH₃ | 4-C≡CH | 1 | |
| 191 | H | CH₃ | CH₃ | CH₃ | 4-(phenyl) | 1 | |
| 192 | H | CH₃ | CH₃ | CH₃ | 2-OCH₃ | 1 | |
| 193 | H | CH₃ | CH₃ | CH₃ | 3-OC₄H₉-i | 1 | |
| 194 | H | CH₃ | CH₃ | CH₃ | 4-OC₂H₅ | 1 | |
| 195 | H | CH₃ | CH₃ | CH₃ | 4-OC₃H₇-n | 1 | |
| 196 | H | CH₃ | CH₃ | CH₃ | 4-OC₄H₉-i | 1 | |
| 197 | H | CH₃ | CH₃ | CH₃ | 3-O-(cyclopentyl-H) | 1 | |
| 198 | H | CH₃ | CH₃ | CH₃ | 3-OCH₂CH=CH₂ | 1 | |
| 199 | H | CH₃ | CH₃ | CH₃ | 3-OCH₂-(phenyl) | 1 | |

TABLE 1-continued structure: Xk-phenyl-C(R)=C(CO-N(R1)(R2)-C-phenyl-Yn with (CH2)m bridge

| Compound No. | Xk | R | R¹ | R² | Yn | m | Melting point (°C.) or refractive index ($n_D^{20}$) |
|---|---|---|---|---|---|---|---|
| 200 | H | CH₃ | CH₃ | CH₃ | 3-O-phenyl | 1 | |
| 201 | 2-F | CH₃ | CH₃ | CH₃ | 3-O-phenyl | 1 | |
| 202 | H | CH₃ | CH₃ | CH₃ | 4-O-phenyl | 1 | |
| 203 | 2-F | CH₃ | CH₃ | CH₃ | 3-OCHF₂ | 1 | |
| 204 | H | CH₃ | CH₃ | CH₃ | 3-OCF₃ | 1 | |
| 205 | 2-F | CH₃ | CH₃ | CH₃ | 3-OCF₃ | 1 | |
| 206 | H | CH₃ | CH₃ | CH₃ | 4-OCF₃ | 1 | |
| 207 | H | CH₃ | CH₃ | CH₃ | 3-OCF₂CHFCl | 1 | |
| 208 | H | CH₃ | CH₃ | CH₃ | 3-OCF₂CHFCF₃ | 1 | |
| 209 | H | CH₃ | CH₃ | CH₃ | 3-OCH₂CH₂OCH₃ | 1 | |
| 210 | H | H | CH₃ | CH₃ | 3-OCH₂COOCH₃ | 1 | |
| 211 | H | CH₃ | CH₃ | CH₃ | 3-OH | 1 | |
| 212 | H | CH₃ | CH₃ | CH₃ | 3-SCH₃ | 1 | |
| 213 | 2-F | CH₃ | CH₃ | CH₃ | 3-SCH₃ | 1 | |
| 214 | H | CH₃ | CH₃ | CH₃ | 3-SC₂H₅ | 1 | |
| 215 | H | CH₃ | CH₃ | CH₃ | 3-SC₄H₉-i | 1 | |
| 216 | H | CH₃ | CH₃ | CH₃ | 4-SCH₃ | 1 | |
| 217 | H | CH₃ | CH₃ | CH₃ | 4-SC₂H₅ | 1 | |
| 218 | H | CH₃ | CH₃ | CH₃ | 3-cyclopropyl | 1 | |
| 219 | H | CH₃ | CH₃ | CH₃ | 3-SCH₂CH=CHCH₃ | 1 | |
| 220 | H | CH₃ | CH₃ | CH₃ | 3-SCH₂C≡CH | 1 | |
| 221 | H | CH₃ | CH₃ | CH₃ | 3-SCH₂-phenyl | 1 | |
| 222 | H | CH₃ | CH₃ | CH₃ | 3-S-phenyl | 1 | |
| 223 | 2-F | CH₃ | CH₃ | CH₃ | 3-S-phenyl | 1 | |
| 224 | H | CH₃ | CH₃ | CH₃ | 3-SCHF₂ | 1 | |
| 225 | H | CH₃ | CH₃ | CH₃ | 3-NH₂ | 1 | |
| 226 | H | CH₃ | CH₃ | CH₃ | 4-NH₂ | 1 | |
| 227 | H | CH₃ | CH₃ | CH₃ | 3-NHCH₃ | 1 | |
| 228 | H | CH₃ | CH₃ | CH₃ | 4-NHCH₃ | 1 | |
| 229 | H | CH₃ | CH₃ | CH₃ | 3-N(CH₃)₂ | 1 | |
| 230 | H | CH₃ | CH₃ | CH₃ | 4-N(CH₃)₂ | 1 | |
| 231 | H | CH₃ | CH₃ | CH₃ | 3-SO₂CH₃ | 1 | |
| 232 | 2-F | CH₃ | CH₃ | CH₃ | 3-SO₂CH₃ | 1 | |
| 233 | H | CH₃ | CH₃ | CH₃ | 4-SO₂CH₃ | 1 | |
| 234 | H | CH₃ | CH₃ | CH₃ | 3-SO₂N(CH₃)₂ | 1 | |
| 235 | H | CH₃ | CH₃ | CH₃ | 3-COOH | 1 | |

TABLE 1-continued

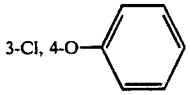

| Compound No. | Xk | R | R¹ | R² | Yn | m | Melting point (°C.) or refractive index ($n_D^{20}$) |
|---|---|---|---|---|---|---|---|
| 236 | H | CH₃ | CH₃ | CH₃ | 3-COOCH₃ | 1 | |
| 237 | H | CH₃ | CH₃ | CH₃ | 3-COOC₂H₅ | 1 | |
| 238 | H | CH₃ | CH₃ | CH₃ | 3-COCH₃ | 1 | |
| 239 | H | CH₃ | CH₃ | CH₃ | 4-COCH₃ | 1 | |
| 240 | H | CH₃ | CH₃ | CH₃ | 4-CN | 1 | |
| 241 | H | CH₃ | CH₃ | CH₃ | 4-NO₂ | 1 | |
| 242 | 3,4-F₂ | CH₃ | CH₃ | CH₃ | 3,4-Cl₂ | 1 | |
| 243 | H | CH₃ | CH₃ | CH₃ | 3-F, 4-CH₃ | 1 | |
| 244 | 2-Cl | CH₃ | CH₃ | CH₃ | 3-F, 4-CH₃ | 1 | |
| 245 | H | CH₃ | CH₃ | CH₃ | 3-Cl, 4-CH₃ | 1 | |
| 246 | 2-F | CH₃ | CH₃ | CH₃ | 3-Cl, 4-CH₃ | 1 | |
| 247 | H | CH₃ | CH₃ | CH₃ | 3-Br, 4-CH₃ | 1 | |
| 248 | 2-F | CH₃ | CH₃ | CH₃ | 3-Br, 4-CH₃ | 1 | |
| 249 | H | CH₃ | CH₃ | CH₃ | 3-I, 4-CH₃ | 1 | |
| 250 | 2-F | CH₃ | CH₃ | CH₃ | 3-I, 4-CH₃ | 1 | |
| 251 | H | CH₃ | CH₃ | CH₃ | 3-Cl, 4-OCH₃ | 1 | |
| 252 | 2-F | CH₃ | CH₃ | CH₃ | 3-Cl, 4-OCH₃ | 1 | |
| 253 | 2,6-F₂ | CH₃ | CH₃ | CH₃ | 3-Cl, 4-OCH₃ | 1 | |
| 254 | H | CH₃ | CH₃ | CH₃ | 3-Cl, 4-OCH₂CH=C(CH₃)₂ | 1 | |
| 255 | H | CH₃ | CH₃ | CH₃ | 3-Cl, 4-OCH₂CH₂OCH₃ | 1 | |
| 256 | H | CH₃ | CH₃ | CH₃ | 3-Cl, 4-OCH(CH₃)COOCH₃ | 1 | |
| 257 | H | CH₃ | CH₃ | CH₃ | 3-Cl, 4-O—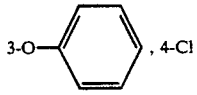 | 1 | |
| 258 | H | CH₃ | CH₃ | CH₃ | 3-Cl, 4-OH | 1 | |
| 259 | H | CH₃ | CH₃ | CH₃ | 3-O—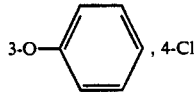, 4-Cl | 1 | |
| 260 | 2-F | CH₃ | CH₃ | CH₃ | 3-O—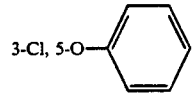, 4-Cl | 1 | |
| 261 | H | CH₃ | CH₃ | CH₃ | 3,4-(OCH₃)₂ | 1 | |
| 262 | H | CH₃ | CH₃ | CH₃ | 3,4-(OC₂H₅)₂ | 1 | |
| 262 | 2-F | CH₃ | CH₃ | CH₃ | 3,5-Cl₂ | 1 | |
| 263 | 2-Br | CH₃ | CH₃ | CH₃ | 3,5-Cl₂ | 1 | |
| 264 | 2-OCHF₂ | CH₃ | CH₃ | CH₃ | 3,5-Cl₂ | 1 | |
| 265 | 2-SCH₃ | CH₃ | CH₃ | CH₃ | 3,5-Cl₂ | 1 | |
| 266 | 3-NO₂ | CH₃ | CH₃ | CH₃ | 3,5-Cl₂ | 1 | |
| 267 | 2,6-F₂ | CH₃ | CH₃ | CH₃ | 3,5-Cl₂ | 1 | |
| 268 | 2-Cl, 6-F | CH₃ | CH₃ | CH₃ | 3,5-Cl₂ | 1 | |
| 269 | H | CH₃ | CH₃ | CH₃ | 3-Cl, 5-OCH₃ | 1 | |
| 270 | 2-F | CH₃ | CH₃ | CH₃ | 3-Cl, 5-OCH₃ | 1 | |
| 271 | H | CH₃ | CH₃ | CH₃ | 3-Cl, 5-OCHF₂ | 1 | |
| 272 | 2-F | CH₃ | CH₃ | CH₃ | 3-Cl, 5-OCHF₂ | 1 | |
| 273 | 2-F | CH₃ | CH₃ | CH₃ | 3,5-(OCHF₂)₂ | 1 | |
| 274 | H | CH₃ | CH₃ | CH₃ | 3-Cl, 5-O—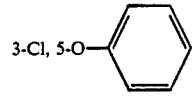 | 1 | |
| 275 | 2-F | CH₃ | CH₃ | CH₃ | 3-Cl, 5-O— | 1 | |

TABLE 1-continued

[Structure diagram with formula showing X_k-phenyl connected to C=C(R)(CH2)m-N-C(R1)(R2)-phenyl-Yn, with C=O group]

| Compound No. | Xk | R | R¹ | R² | Yn | m | Melting point (°C.) or refractive index ($n_D^{20}$) |
|---|---|---|---|---|---|---|---|
| 276 | H | CH₃ | CH₃ | CH₃ | 3-Br, 5-O-phenyl | 1 | |
| 278 | 2-F | CH₃ | CH₃ | CH₃ | 3-Br, 5-O-phenyl | 1 | |
| 279 | H | CH₃ | CH₃ | CH₃ | 3,5-(O-phenyl)₂ | 1 | |
| 280 | 2-F | CH₃ | CH₃ | CH₃ | 3,5-(O-phenyl)₂ | 1 | |
| 281 | H | CH₃ | CH₃ | CH₃ | 3,5-Cl₂, 4-CH₃ | 1 | |
| 282 | 2-F | CH₃ | CH₃ | CH₃ | 3,5-Cl₂, 4-CH₃ | 1 | |
| 283 | H | CH₃ | CH₃ | CH₃ | 3,5-Cl₂, 2-OCH₃ | 1 | |
| 284 | H | CH₃ | CH₃ | CH₃ | 3,5-Cl₂, 4-OCH₃ | 1 | |
| 285 | 2-F | CH₃ | CH₃ | CH₃ | 3,5-Cl₂, 4-OCH₃ | 1 | |
| 286 | 2-Cl | CH₃ | CH₃ | CH₃ | 3,5-Cl₂, 4-OCH₃ | 1 | |
| 287 | 2-CH₃ | CH₃ | CH₃ | CH₃ | 3,5-Cl₂, 4-OCH₃ | 1 | |
| 288 | 2,5-F₂ | CH₃ | CH₃ | CH₃ | 3,5-Cl₂, 4-OC₂H₅ | 1 | |
| 290 | H | CH₃ | CH₃ | CH₃ | 3,5-Cl₂, 4-OC₃H₇-n | 1 | |
| 291 | H | CH₃ | CH₃ | CH₃ | 3,5-Cl₂, 4-O-cyclopropyl | 1 | |
| 292 | H | CH₃ | CH₃ | CH₃ | 3,5-Br₂, 4-OCH₃ | 1 | |
| 293 | 2-F | CH₃ | CH₃ | CH₃ | 3,5-Br₂, 4-OCH₃ | 1 | |
| 294 | H | CH₃ | CH₃ | CH₃ | 3,5-Cl₂, 4-OCH₂CH=CH₂ | 1 | |
| 295 | H | CH₃ | CH₃ | CH₃ | 3,5-Cl₂, 4-OCH₂C≡CH | 1 | |
| 296 | H | CH₃ | CH₃ | CH₃ | 3,5-Cl₂, 4-OCHF₂ | 1 | |
| 297 | H | CH₃ | CH₃ | CH₃ | 3,5-Cl₂, 4-OCH₂CF₃ | 1 | |
| 298 | H | CH₃ | CH₃ | CH₃ | 3,5-Cl₂, 4-OCF₂CHFCl | 1 | |
| 299 | H | CH₃ | CH₃ | CH₃ | 3,5-Br₂, 4-OCHF₂ | 1 | |
| 300 | H | CH₃ | CH₃ | CH₃ | 3,5-Cl₂, 4-OCH₂CN | 1 | |
| 301 | H | CH₃ | CH₃ | CH₃ | 3,5-Cl₂, 4-OCH₂-phenyl | 1 | |
| 302 | H | CH₃ | CH₃ | CH₃ | 3,5-Cl₂, 4-OCH₂CH₂OCH₃ | 1 | |
| 303 | H | CH₃ | CH₃ | CH₃ | 3,5-Cl₂, 4-OCH₂COOCH₃ | 1 | |
| 304 | H | CH₃ | CH₃ | CH₃ | 3,5-Cl₂, 4-OCH(CH₃)COOCH₃ | 1 | |
| 305 | H | CH₃ | CH₃ | CH₃ | 3,5-Cl₂, 4-OH | 1 | |
| 306 | H | CH₃ | CH₃ | CH₃ | 3,5-Cl₂, 4-SCH₃ | 1 | |
| 307 | 2-F | CH₃ | CH₃ | CH₃ | 3,5-Cl₂, 4-SCH₃ | 1 | |
| 308 | H | CH₃ | CH₃ | CH₃ | 3,5-Cl₂, 4-SC₂H₅ | 1 | |
| 309 | H | CH₃ | CH₃ | CH₃ | 3,5-Cl₂, 4-SCH₂CH=CH₂ | 1 | |
| 310 | H | CH₃ | CH₃ | CH₃ | 3,5-Cl₂, 4-SCH₂C≡CH | 1 | |
| 311 | 2-F | CH₃ | CH₃ | CH₃ | 3,5-Cl₂, 4-SCH₂C≡CH | 1 | |
| 312 | H | CH₃ | CH₃ | CH₃ | 3,5-Cl₂, 4-SCH₂COOC₂H₅ | 1 | |
| 313 | H | CH₃ | CH₃ | CH₃ | 3,5-Cl₂, 4-NH₂ | 1 | |
| 314 | H | CH₃ | CH₃ | CH₃ | 3,5-Cl₂, 4-N(CH₃)₂ | 1 | |
| 315 | H | CH₃ | CH₃ | CH₃ | 3,5-Cl₂, 4-SO₂N(CH₃)₂ | 1 | |
| 316 | 2-F | CH₃ | CH₃ | CH₃ | 3,5-Cl₂, 4-SO₂N(CH₃)₂ | 1 | |
| 317 | H | CH₃ | CH₃ | CH₃ | 3,5-(CH₃)₂,4-OCH₃ | 1 | |

TABLE 1-continued

| Compound No. | Xk | R | R¹ | R² | Yn | m | Melting point (°C.) or refractive index ($n_D^{20}$) |
|---|---|---|---|---|---|---|---|
| 318 | H | CH₃ | CH₃ | CH₃ | 3,4,5-(OCH₃)₃ | 1 | |
| 319 | 2-F | H | CH₃ | CH₃ | 3,5-Cl₂ | 0 | |
| 320 | H | H | CH₃ | CH₃ | 3,5-Cl₂, 4-OCH₃ | 0 | |
| 321 | 2-OCHF₂ | CH₃ | CH₃ | CH₃ | 3-F | 0 | |
| 322 | 2,6-Cl₂ | CH₃ | CH₃ | CH₃ | 3-F | 0 | 114–116 |
| 323 | 2-CH₃ | CH₃ | CH₃ | CH₃ | 3-Cl | 0 | |
| 324 | 2-CF₃ | CH₃ | CH₃ | CH₃ | 3-Cl | 0 | |
| 325 | 2,6-F₂ | CH₃ | CH₃ | CH₃ | 3-Cl | 0 | |
| 326 | 2,6-Cl₂ | CH₃ | CH₃ | CH₃ | 3-Cl | 0 | 130–134 |
| 327 | 2-F | CH₃ | CH₃ | CH₃ | 3-Br | 0 | |
| 328 | 2-F | CH₃ | CH₃ | CH₃ | 3-I | 0 | |
| 329 | 2-Cl | CH₃ | CH₃ | CH₃ | 3-CH₃ | 0 | |
| 330 | H | CH₃ | CH₃ | CH₃ | 3-C₂H₅ | 0 | |
| 331 | H | CH₃ | CH₃ | CH₃ | 4-C₂H₅ | 0 | |
| 332 | H | CH₃ | CH₃ | CH₃ | 4-C₃H₇-n | 0 | |
| 333 | H | CH₃ | CH₃ | CH₃ | 4-C₃H₇-i | 0 | |
| 334 | H | CH₃ | CH₃ | CH₃ | 4-C₄H₉-n | 0 | |
| 335 | H | CH₃ | CH₃ | CH₃ | 4-C₄H₉-t | 0 | |
| 336 | H | CH₃ | CH₃ | CH₃ | 4-C₅H₁₁-n | 0 | |
| 337 | H | CH₃ | CH₃ | CH₃ | 4-(cyclohexyl-H) | 0 | |
| 338 | H | CH₃ | CH₃ | CH₃ | 3-C(CH₃)=CH₂ | 0 | |
| 339 | H | CH₃ | CH₃ | CH₃ | 4-CH=CH₂ | 0 | |
| 340 | H | CH₃ | CH₃ | CH₃ | 4-C(CH₃)=CH₂ | 0 | |
| 341 | H | CH₃ | CH₃ | CH₃ | 3-C≡CH | 0 | |
| 342 | H | CH₃ | CH₃ | CH₃ | 4-C≡CH | 0 | |
| 343 | H | CH₃ | CH₃ | CH₃ | 4-(phenyl) | 0 | |
| 344 | H | CH₃ | CH₃ | CH₃ | 2-OCH₃ | 0 | |
| 345 | H | CH₃ | CH₃ | CH₃ | 3-OC₄H₉-i | 0 | |
| 346 | H | CH₃ | CH₃ | CH₃ | 4-OC₂H₅ | 0 | |
| 347 | H | CH₃ | CH₃ | CH₃ | 4-OC₃H₇-n | 0 | |
| 348 | H | CH₃ | CH₃ | CH₃ | 4-OC₄H₉-i | 0 | |
| 349 | H | CH₃ | CH₃ | CH₃ | 3-O-(cyclopentyl-H) | 0 | |
| 350 | H | CH₃ | CH₃ | CH₃ | 3-OCH₂CH=CH₂ | 0 | |
| 351 | H | CH₃ | CH₃ | CH₃ | 3-OCH₂(phenyl) | 0 | 111–112 |
| 352 | H | CH₃ | CH₃ | CH₃ | 3-O(phenyl) | 0 | 125–126 |
| 353 | 2-F | CH₃ | CH₃ | CH₃ | 3-O(phenyl) | 0 | |

TABLE 1-continued

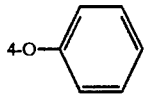

| Compound No. | Xk | R | R¹ | R² | Yn | m | Melting point (°C.) or refractive index ($n_D^{20}$) |
|---|---|---|---|---|---|---|---|
| 354 | H | $CH_3$ | $CH_3$ | $CH_3$ | 4-O-phenyl | 0 | 99–100 |
| 355 | 2-F | $CH_3$ | $CH_3$ | $CH_3$ | 3-$OCHF_2$ | 0 | |
| 356 | H | $CH_3$ | $CH_3$ | $CH_3$ | 3-$OCF_3$ | 0 | |
| 357 | 2-F | $CH_3$ | $CH_3$ | $CH_3$ | 3-$OCF_3$ | 0 | |
| 358 | H | $CH_3$ | $CH_3$ | $CH_3$ | 4-$OCF_3$ | 0 | 1.5479 |
| 359 | H | $CH_3$ | $CH_3$ | $CH_3$ | 3-$OCF_2CHFCl$ | 0 | |
| 360 | H | $CH_3$ | $CH_3$ | $CH_3$ | 3-$OCF_2CHFCF_3$ | 0 | |
| 361 | H | $CH_3$ | $CH_3$ | $CH_3$ | 3-$OCH_2CH_2OCH_3$ | 0 | |
| 362 | H | H | $CH_3$ | $CH_3$ | 3-$OCH_2COOCH_3$ | 0 | 1.5790 |
| 363 | H | $CH_3$ | $CH_3$ | $CH_3$ | 3-OH | 0 | 163–166 |
| 364 | H | $CH_3$ | $CH_3$ | $CH_3$ | 3-$SCH_3$ | 0 | Not measurable |
| 365 | 2-F | $CH_3$ | $CH_3$ | $CH_3$ | 3-$SCH_3$ | 0 | Not measurable |
| 366 | H | $CH_3$ | $CH_3$ | $CH_3$ | 3-$SC_2H_5$ | 0 | |
| 367 | H | $CH_3$ | $CH_3$ | $CH_3$ | 3-$SC_4H_9$-i | 0 | |
| 368 | H | $CH_3$ | $CH_3$ | $CH_3$ | 4-$SCH_3$ | 0 | Not measurable |
| 369 | H | $CH_3$ | $CH_3$ | $CH_3$ | 4-$SC_2H_5$ | 0 | |
| 370 | H | $CH_3$ | $CH_3$ | $CH_3$ | 3-cyclopropyl | 0 | |
| 371 | H | $CH_3$ | $CH_3$ | $CH_3$ | 3-$SCH_2CH=CHCH_3$ | 0 | |
| 372 | H | $CH_3$ | $CH_3$ | $CH_3$ | 3-$SCH_2C\equiv CH$ | 0 | |
| 373 | H | $CH_3$ | $CH_3$ | $CH_3$ | 3-$SCH_2$-phenyl | 0 | |
| 374 | H | $CH_3$ | $CH_3$ | $CH_3$ | 3-S-phenyl | 0 | Not measurable |
| 375 | 2-F | $CH_3$ | $CH_3$ | $CH_3$ | 3-S-phenyl | 0 | |
| 376 | H | $CH_3$ | $CH_3$ | $CH_3$ | 3-$SCHF_2$ | 0 | |
| 377 | H | $CH_3$ | $CH_3$ | $CH_3$ | 3-$NH_2$ | 0 | |
| 378 | H | $CH_3$ | $CH_3$ | $CH_3$ | 4-$NH_2$ | 0 | 140–142 |
| 379 | H | $CH_3$ | $CH_3$ | $CH_3$ | 3-$NHCH_3$ | 0 | |
| 380 | H | $CH_3$ | $CH_3$ | $CH_3$ | 4-$NHCH_3$ | 0 | |
| 381 | H | $CH_3$ | $CH_3$ | $CH_3$ | 3-$N(CH_3)_2$ | 0 | |
| 382 | H | $CH_3$ | $CH_3$ | $CH_3$ | 4-$N(CH_3)_2$ | 0 | |
| 383 | H | $CH_3$ | $CH_3$ | $CH_3$ | 3-$SO_2CH_3$ | 0 | 162–164 |
| 384 | 2-F | $CH_3$ | $CH_3$ | $CH_3$ | 3-$SO_2CH_3$ | 0 | 125–128 |
| 385 | H | $CH_3$ | $CH_3$ | $CH_3$ | 4-$SO_2CH_3$ | 0 | 154–160 |
| 386 | H | $CH_3$ | $CH_3$ | $CH_3$ | 3-$SO_2N(CH_3)_2$ | 0 | |
| 387 | H | $CH_3$ | $CH_3$ | $CH_3$ | 3-COOH | 0 | |
| 388 | H | $CH_3$ | $CH_3$ | $CH_3$ | 3-$COOCH_3$ | 0 | |
| 389 | H | $CH_3$ | $CH_3$ | $CH_3$ | 4-$COOC_2H_5$ | 0 | 1.5859 |
| 390 | H | $CH_3$ | $CH_3$ | $CH_3$ | 3-$COCH_3$ | 0 | |
| 391 | H | $CH_3$ | $CH_3$ | $CH_3$ | 4-$COCH_3$ | 0 | 98–102 |
| 392 | H | $CH_3$ | $CH_3$ | $CH_3$ | 4-CN | 0 | 145–148 |
| 393 | H | $CH_3$ | $CH_3$ | $CH_3$ | 4-$NO_2$ | 0 | 123–126 |
| 394 | 3,4-$F_2$ | $CH_3$ | $CH_3$ | $CH_3$ | 3,4-$Cl_2$ | 0 | |
| 395 | H | $CH_3$ | $CH_3$ | $CH_3$ | 3-F, 4-$CH_3$ | 0 | |
| 396 | 2-Cl | $CH_3$ | $CH_3$ | $CH_3$ | 3-F, 4-$CH_3$ | 0 | |
| 397 | H | $CH_3$ | $CH_3$ | $CH_3$ | 3-Cl, 4-$CH_3$ | 0 | |
| 398 | 2-F | $CH_3$ | $CH_3$ | $CH_3$ | 3-Cl, 4-$CH_3$ | 0 | |
| 399 | H | $CH_3$ | $CH_3$ | $CH_3$ | 3-Br, 4-$CH_3$ | 0 | |

TABLE 1-continued

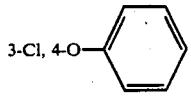

| Compound No. | Xk | R | R¹ | R² | Yn | m | Melting point (°C.) or refractive index ($n_D^{20}$) |
|---|---|---|---|---|---|---|---|
| 400 | 2-F | $CH_3$ | $CH_3$ | $CH_3$ | 3-Br, 4-$CH_3$ | 0 | |
| 401 | H | $CH_3$ | $CH_3$ | $CH_3$ | 3-I, 4-$CH_3$ | 0 | |
| 402 | 2-F | $CH_3$ | $CH_3$ | $CH_3$ | 3-I, 4-$CH_3$ | 0 | |
| 403 | H | $CH_3$ | $CH_3$ | $CH_3$ | 3-Cl, 4-$OCH_3$ | 0 | Not measurable |
| 404 | 2-F | $CH_3$ | $CH_3$ | $CH_3$ | 3-Cl, 4-$OCH_3$ | 0 | |
| 405 | 2,6-$F_2$ | $CH_3$ | $CH_3$ | $CH_3$ | 3-Cl, 4-$OCH_3$ | 0 | |
| 406 | H | $CH_3$ | $CH_3$ | $CH_3$ | 3-Cl, 4-$OCH_2CH=C(CH_3)_2$ | 0 | |
| 407 | H | $CH_3$ | $CH_3$ | $CH_3$ | 3-Cl, 4-$OCH_2CH_2OCH_3$ | 0 | |
| 408 | H | $CH_3$ | $CH_3$ | $CH_3$ | 3-Cl, 4-$OCH(CH_3)COOCH_3$ | 0 | |
| 409 | H | $CH_3$ | $CH_3$ | $CH_3$ | 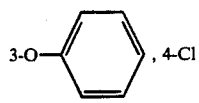 3-Cl, 4-O— | 0 | 131–133 |
| 410 | H | $CH_3$ | $CH_3$ | $CH_3$ | 3-Cl, 4-OH | 0 | |
| 411 | H | $CH_3$ | $CH_3$ | $CH_3$ | 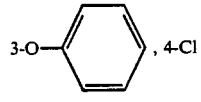 3-O—, 4-Cl | 0 | |
| 412 | 2-F | $CH_3$ | $CH_3$ | $CH_3$ | 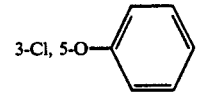 3-O—, 4-Cl | 0 | |
| 413 | H | $CH_3$ | $CH_3$ | $CH_3$ | 3,4-$(OCH_3)_2$ | 0 | |
| 414 | H | $CH_3$ | $CH_3$ | $CH_3$ | 3,4-$(OC_2H_5)_2$ | 0 | |
| 415 | 2-Br | $CH_3$ | $CH_3$ | $CH_3$ | 3,5-$Cl_2$ | 0 | |
| 416 | 2-$OCHF_2$ | $CH_3$ | $CH_3$ | $CH_3$ | 3,5-$Cl_2$ | 0 | |
| 417 | 2-$SCH_3$ | $CH_3$ | $CH_3$ | $CH_3$ | 3,5-$Cl_2$ | 0 | |
| 418 | 3-$NO_2$ | $CH_3$ | $CH_3$ | $CH_3$ | 3,5-$Cl_2$ | 0 | |
| 419 | 2,6-$F_2$ | $CH_3$ | $CH_3$ | $CH_3$ | 3,5-$Cl_2$ | 0 | |
| 420 | 2-Cl, 6-F | $CH_3$ | $CH_3$ | $CH_3$ | 3,5-$Cl_2$ | 0 | |
| 421 | H | $CH_3$ | $CH_3$ | $CH_3$ | 3-Cl, 5-$OCH_3$ | 0 | |
| 422 | 2-F | $CH_3$ | $CH_3$ | $CH_3$ | 3-Cl, 5-$OCH_3$ | 0 | |
| 423 | H | $CH_3$ | $CH_3$ | $CH_3$ | 3-Cl, 5-$OCHF_2$ | 0 | |
| 424 | 2-F | $CH_3$ | $CH_3$ | $CH_3$ | 3-Cl, 5-$OCHF_2$ | 0 | |
| 425 | 2-F | $CH_3$ | $CH_3$ | $CH_3$ | 3,5-$(OCHF_2)_2$ | 0 | |
| 426 | H | $CH_3$ | $CH_3$ | $CH_3$ | 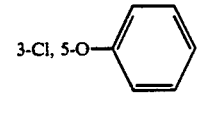 3-Cl, 5-O— | 0 | 144–148 |
| 427 | 2-F | $CH_3$ | $CH_3$ | $CH_3$ | 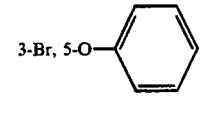 3-Cl, 5-O— | 0 | |
| 428 | H | $CH_3$ | $CH_3$ | $CH_3$ | 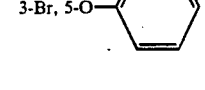 3-Br, 5-O— | 0 | 139–143 |
| 429 | 2-F | $CH_3$ | $CH_3$ | $CH_3$ | 3-Br, 5-O— | 0 | |

TABLE 1-continued

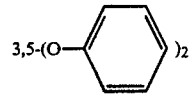

| Compound No. | Xk | R | R¹ | R² | Yn | m | Melting point (°C.) or refractive index ($n_D^{20}$) |
|---|---|---|---|---|---|---|---|
| 430 | H | $CH_3$ | $CH_3$ | $CH_3$ | 3,5-(O—Ph)₂ | 0 | |
| 431 | 2-F | $CH_3$ | $CH_3$ | $CH_3$ | 3,5-(O—Ph)₂ | 0 | |
| 432 | H | $CH_3$ | $CH_3$ | $CH_3$ | 3,5-$Cl_2$, 4-$CH_3$ | 0 | |
| 433 | 2-F | $CH_3$ | $CH_3$ | $CH_3$ | 3,5-$Cl_2$, 4-$CH_3$ | 0 | |
| 434 | H | $CH_3$ | $CH_3$ | $CH_3$ | 3,5-$Cl_2$, 2-$OCH_3$ | 0 | |
| 435 | 2-Cl | $CH_3$ | $CH_3$ | $CH_3$ | 3,5-$Cl_2$, 4-$OCH_3$ | 0 | 132–135 |
| 436 | 2-$CH_3$ | $CH_3$ | $CH_3$ | $CH_3$ | 3,5-$Cl_2$, 4-$OCH_3$ | 0 | |
| 437 | 2,5-$F_2$ | $CH_3$ | $CH_3$ | $CH_3$ | 3,5-$Cl_2$, 4-$OCH_3$ | 0 | |
| 438 | H | $CH_3$ | $CH_3$ | $CH_3$ | 3,5-$Cl_2$, 4-$OC_2H_5$ | 0 | 133–135 |
| 439 | H | $CH_3$ | $CH_3$ | $CH_3$ | 3,5-$Cl_2$, 4-$OC_3H_7$-n | 0 | 150–153 |
| 440 | H | $CH_3$ | $CH_3$ | $CH_3$ | 3,5-$Cl_2$, 4-O—△ | 0 | |
| 441 | H | $CH_3$ | $CH_3$ | $CH_3$ | 3,5-$Br_2$, 4-$OCH_3$ | 0 | |
| 442 | 2-F | $CH_3$ | $CH_3$ | $CH_3$ | 3,5-$Br_2$, 4-$OCH_3$ | 0 | |
| 443 | H | $CH_3$ | $CH_3$ | $CH_3$ | 3,5-$Cl_2$, 4-$OCH_2CH=CH_2$ | 0 | 137–140 |
| 444 | H | $CH_3$ | $CH_3$ | $CH_3$ | 3,5-$Cl_2$, 4-$OCH_2C\equiv CH$ | 0 | 163–165 |
| 445 | H | $CH_3$ | $CH_3$ | $CH_3$ | 3,5-$Cl_2$, 4-$OCH_2CF_3$ | 0 | |
| 446 | H | $CH_3$ | $CH_3$ | $CH_3$ | 3,5-$Cl_2$, 4-$OCF_2CHFCl$ | 0 | |
| 447 | H | $CH_3$ | $CH_3$ | $CH_3$ | 3,5-$Br_2$, 4-$OCHF_2$ | 0 | |
| 448 | H | $CH_3$ | $CH_3$ | $CH_3$ | 3,5-$Cl_2$, 4-$OCH_2CN$ | 0 | 163–168 |
| 449 | H | $CH_3$ | $CH_3$ | $CH_3$ | 3,5-$Cl_2$, 4-$OCH_2$—Ph | 0 | 108–111 |
| 450 | H | $CH_3$ | $CH_3$ | $CH_3$ | 3,5-$Cl_2$, 4-$OCH_2OCH_3$ | 0 | 144–146 |
| 451 | H | $CH_3$ | $CH_3$ | $CH_3$ | 3,5-$Cl_2$, 4-$OCH_2COOCH_3$ | 0 | |
| 452 | H | $CH_3$ | $CH_3$ | $CH_3$ | 3,5-$Cl_2$, 4-$OCH(CH_3)COOC_2H_5$ | 0 | 130–132 |
| 453 | H | $CH_3$ | $CH_3$ | $CH_3$ | 3,5-$Cl_2$, 4-OH | 0 | 224–227 |
| 454 | H | $CH_3$ | $CH_3$ | $CH_3$ | 3,5-$Cl_2$, 4-$SCH_3$ | 0 | 109–110 |
| 455 | 2-F | $CH_3$ | $CH_3$ | $CH_3$ | 3,5-$Cl_2$, 4-$SCH_3$ | 0 | 130–132 |
| 456 | H | $CH_3$ | $CH_3$ | $CH_3$ | 3,5-$Cl_2$, 4-$SC_2H_5$ | 0 | |
| 457 | H | $CH_3$ | $CH_3$ | $CH_3$ | 3,5-$Cl_2$, 4-$SCH_2CH=CH_2$ | 0 | |
| 458 | H | $CH_3$ | $CH_3$ | $CH_3$ | 3,5-$Cl_2$, 4-$SCH_2C\equiv CH$ | 0 | |
| 459 | 2-F | $CH_3$ | $CH_3$ | $CH_3$ | 3,5-$Cl_2$, 4-$SCH_2C\equiv CH$ | 0 | |
| 460 | H | $CH_3$ | $CH_3$ | $CH_3$ | 3,5-$Cl_2$, 4-$SCH_2COOC_2H_5$ | 0 | |
| 461 | H | $CH_3$ | $CH_3$ | $CH_3$ | 3,5-$Cl_2$, 4-$NH_2$ | 0 | |
| 462 | H | $CH_3$ | $CH_3$ | $CH_3$ | 3,5-$Cl_2$, 4-$N(CH_3)_2$ | 0 | |
| 463 | H | $CH_3$ | $CH_3$ | $CH_3$ | 3,5-$Cl_2$, 4-$SO_2N(CH_3)_2$ | 0 | |
| 464 | 2-F | $CH_3$ | $CH_3$ | $CH_3$ | 3,5-$Cl_2$, 4-$SO_2N(CH_3)_2$ | 0 | |
| 465 | H | $CH_3$ | $CH_3$ | $CH_3$ | 3,5-$(CH_3)_2$, 4-$OCH_3$ | 0 | |
| 466 | H | $CH_3$ | $CH_3$ | $CH_3$ | 3,4,5-$(OCH_3)_3$ | 0 | |
| 487 | H | $CH_3$ | $CH_3$ | $CH_3$ | 3,5-$Cl_2$; 4-$OCH_2$—△ | 0 | |
| 488 | H | $CH_3$ | $CH_3$ | $CH_3$ | 3,5-$F_2$ | 0 | |
| 469 | H | $CH_3$ | $CH_3$ | $CH_3$ | 2,5-$Cl_2$; 4-$OCH_3$ | 0 | |
| 470 | H | $CH_3$ | $CH_3$ | $CH_3$ | 2,5-$Cl_2$; 4-$CH_3$ | 0 | |
| 471 | H | $CH_3$ | $CH_3$ | $CH_3$ | 2,3,5-$Cl_3$ | 0 | |
| 472 | H | $CH_3$ | $CH_3$ | $CH_3$ | 2,4,5-$Cl_3$ | 0 | |
| 473 | H | $CH_3$ | $CH_3$ | $CH_3$ | 2,5-$(CH_3)_2$ | 0 | |

TABLE 1-continued

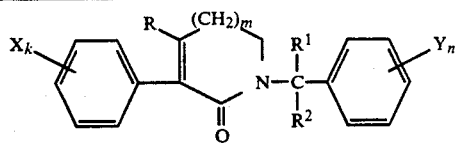

| Compound No. | Xk | R | R¹ | R² | Yn | m | Melting point (°C.) or refractive index ($n_D^{20}$) |
|---|---|---|---|---|---|---|---|
| 474 | H | $CH_3$ | $CH_3$ | $CH_3$ | 2-Cl; 5-$CH_3$ | 0 | |
| 475 | H | $CH_3$ | $CH_3$ | $CH_3$ | 2-Cl; 5-Br | 0 | |
| 476 | H | $CH_3$ | $CH_3$ | $CH_3$ | 2-Br, 5-$OCH_3$ | 0 | |
| 477 | H | $CH_3$ | $CH_3$ | $CH_3$ | 2-$OCH_3$; 5-Cl | 0 | |
| 478 | H | $CH_3$ | $CH_3$ | $CH_3$ | 2,5-$(OCH_3)_2$ | 0 | |
| 479 | H | $CH_3$ | $CH_3$ | $CH_3$ | 2-$OCH_3$; 3-$CH_3$; 5-Cl | 0 | |

Note:
Ph: Phenyl

The compounds of the present invention can be prepared by one of the following processes.

(1) Process for producing the compound of the present invention wherein in the formula I, R is an alkyl group

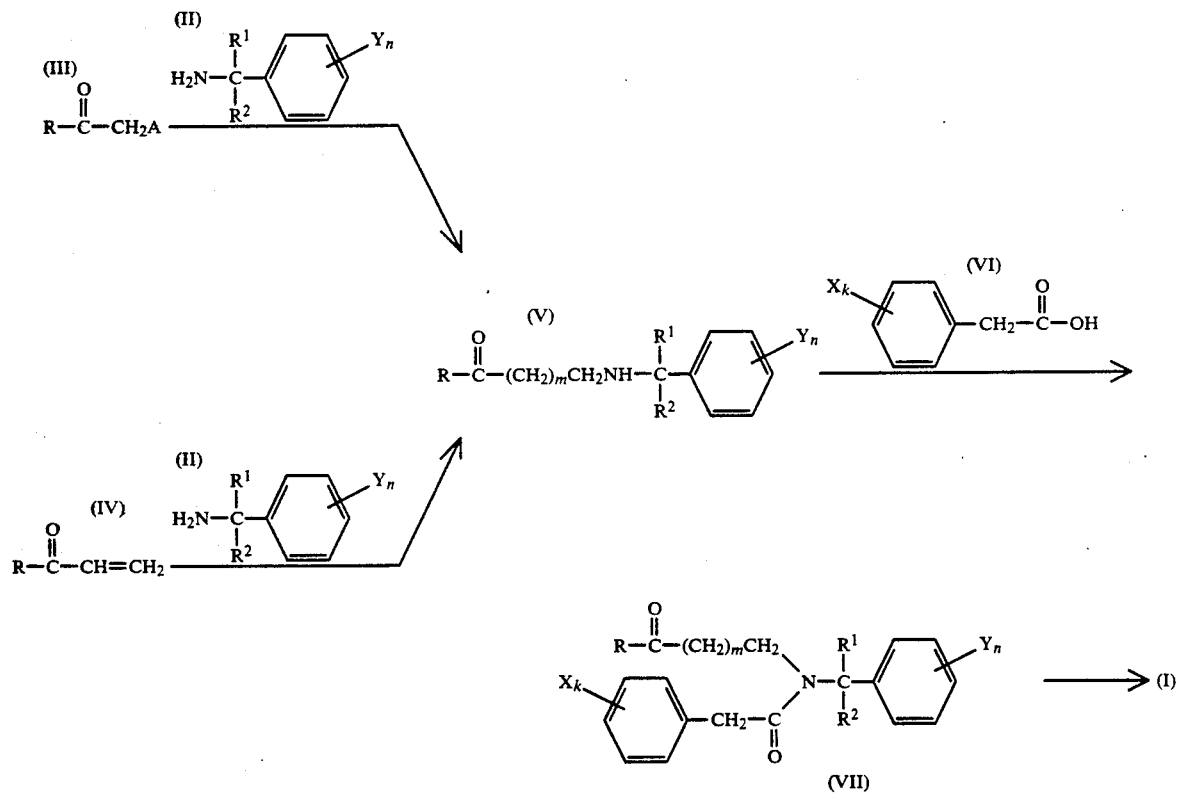

In the above formulas, A is a halogen atom, and X, Y, R¹, R², m, k and n are as defined above.

When m is 0, the benzylamine derivative of the formula II and the compound of the formula III are reacted without a solvent or in a suitable solvent under a nitrogen stream to obtain the intermediate of the formula V in good yield. The reaction successfully proceeds in the presence of a base. The temperature is at at least room temperature, preferably from 50° to 130° C. After completion of the reaction, the intermediate of the formula V can be isolated from the reaction mixture by a usual method. For example, it is obtained by washing the reaction mixture as it is, followed by distillation of the solvent, or the reaction mixture is poured into water and extracted with a water-immicible solvent, and the solvent is distilled off to obtain it. Further, it may be purified by distillation, column chromatography or the like. The solvent to be used in the reaction includes hydrocarbons such as benzene, toluene and xylene, alcohols such as ethyl alcohol and methyl alcohol, ethers such as diethyl ether, dioxane, tetrahydrofuran and dimethoxyethane, halogenated hydrocarbons such as methylene chloride and chloroform, ketones such as acetone and methyl ethyl ketone, and aprotic polar solvents such as acetonitrile, N,N-dimethylformamide, N,N-dimethylacetamide and dimethylsulfoxide. The base to be used includes organic amines such as triethylamine, pyridine, N,N-dimethylaniline, N-methylmorpholine and quinoline, inorganic bases such as sodium hydroxide, potassium hydroxide, sodium carbonate and potassium carbonate, metal alcoholates such as sodium methylate and sodium ethylate, and sodium hydride.

Further, when m is 1, the intermediate of the formula V can be prepared by reacting the benzylamine compound of the formula II with the compound of the formula IV. The reaction of this method is conducted without a solvent or in a suitable solvent under a nitrogen stream. Further, if necessary, a suitable catalyst is used. The reaction is conducted at room temperature or if necessary, under heating or cooling. The reaction is conducted preferably at from 0° to 100° C. After completion of the reaction, the intermediate of the formula V can be isolated by a usual method. For example, compounds having a low boiling point are distilled off under reduced pressure or the reaction mixture is washed with water, and then the solvent was distilled off to obtain it. If necessary, it may be purified by distillation, column chromatography or the like. The organic solvent includes hydrocarbons such as benzene, toluene and xylene, alcohols such as ethyl alcohol and methyl alcohol, ethers such as diethyl ether, dioxane, tetrahydrofuran and dimethoxyethane, and halogenated hydrocarbons such as methylene chloride and chloroform. The catalyst includes organic amines such as triethylamine and pyridine, metal alcoholates such as sodium ethylate, inorganic bases such as potassium carbonate and sodium carbonate, and copper chloride.

Then, the compound of the formula V thereby obtained is dissolved in a suitable organic solvent, and reacted with the reactive derivative of the substituted phenyl acetic acid of the formula VI to obtain the intermediate of the formula VII in good yield. The reaction is conducted at room temperature, or optionally under heating or cooling. The reaction is preferably conducted at from −10° to 50° C. Further, the reaction successfully proceeds in the presence of a base. The base may be added as it is or as an aqueous solution. After completion of the reaction, the intermediate of the formula VII can be isolated from the reaction mixture by a usual method. For example, the reaction mixture is washed with water, and the solvent was distilled off, or the reaction mixture is poured into water and extracted with a water-immicible solvent, and the solvent is distilled off to obtain it. If necessary, it may be purified by recrystallization, distillation, column chromatography or the like. The organic solvent includes hydrocarbons such as benzene, toluene and xylene, ethers such as diethyl ether, dioxane, tetrahydrofuran and dimethoxyethane, halogenated hydrocarbons such as methylene chloride and chloroform, ketones such as acetone and methyl ethyl ketone, and aprotic polar solvents such as acetonitrile, N,N-dimethylformamide and N,N-dimethylacetamide. The reactive derivative of the substituted phenyl acetic acid includes acid anhydride, acid chloride, acid bromide, active esters thereof and the like, which can be readily prepared from the substituted phenyl acetic acid by using a known method. The base includes organic amines such as triethylamine, pyridine, N,N-dimethylaniline, N-methylmorpholine and quinoline, and inorganic bases such as sodium hydroxide, potassium hydroxide, sodium carbonate and potassium carbonate.

The intermediate of the formula VII thereby obtained is subjected to ring closure in a suitable organic solvent to obtain the compound of the present invention wherein in the formula I, R is an alkyl group, in good purity and high yield. The reaction temperature is within a range of from room temperature to the boiling point of the solvent. Further, this reaction successfully, proceeds in the presence of a suitable reaction assistant. After completion of the reaction, the desired compound can be isolated from the reaction mixture by a usual method. For example, the reaction mixture is washed with water, and the solvent is distilled off, or after the distillation of the solvent, water was added to the reaction mixture and the mixture was extracted with a water-immicible organic solvent, and the solvent is distilled off to obtain the desired compound. Further, if necessary, it may be purified by recrystallization, column chromatography or the like. The organic solvent to be used in the reaction includes hydrocarbons such as benzene, toluene and xylene, alcohols such as ethyl alcohol and methyl alcohol, ethers such as dioxane, tetrahydrofuran and dimethoxyethane, halogenated hydrocarbons such as methylene chloride and chloroform, ketones such as acetone and methyl ethyl ketone, and aprotic polar solvents such as acetonitrile, N,N-dimethylformamide, N,N-dimethylacetamide and dimethyl sulfoxide. The reaction assistant includes inorganic bases such as sodium hydroxide, potassium hydroxide, a potassium carbonate and sodium carbonate, and metal alcoholates such as sodium methylate, sodium ethylate and potassium tert-butoxide.

A part of α,α-dimethylbenzylamines among the benzylamine derivative of the formula II which is an intermediate useful for the preparation of the compound of the present invention, are novel compounds, and they can be prepared by the following processes.

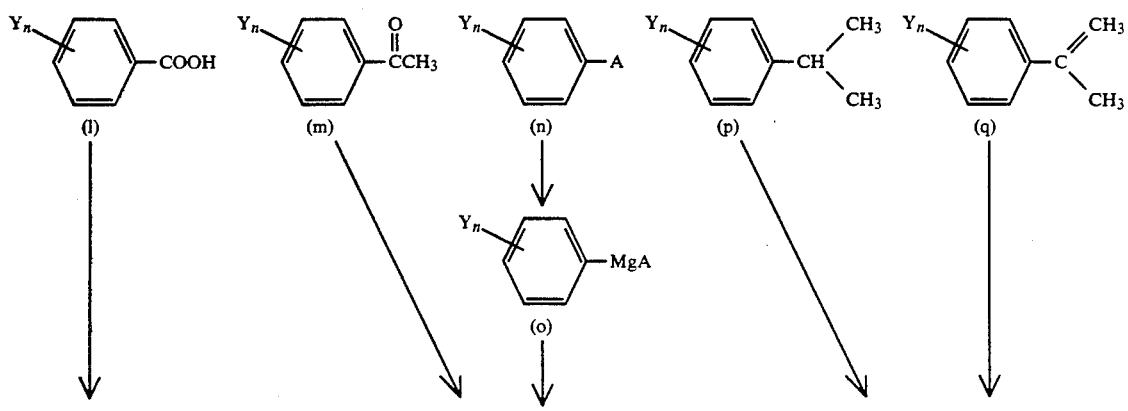

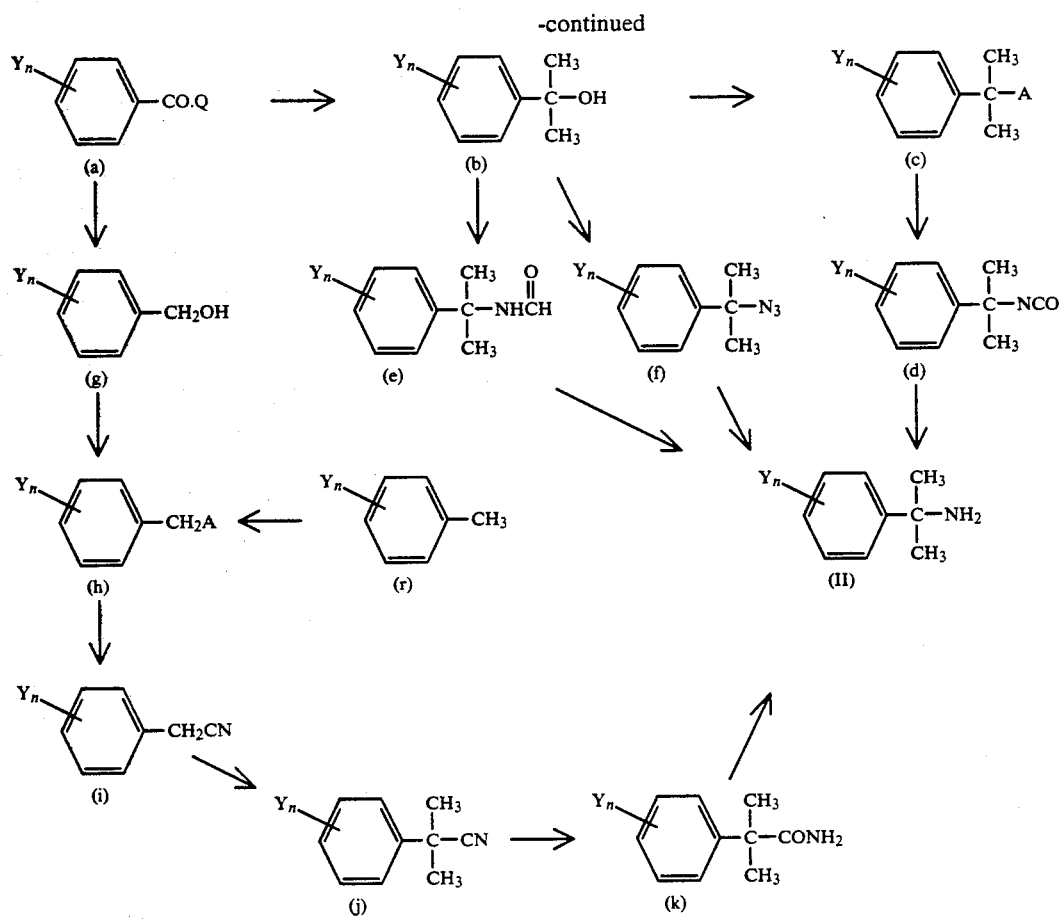

In the above formulas, Q is a halogen atom, an alkoxy group, a benzyloxy group or a phenoxy group, and Y, A and n are as defined above.

Process I

The substituted α,α-dimethylbenzyl alcohol of the formula b can be obtained by reacting the substituted benzoyl halide or substituted-benzoate of the formula a with a methyl magnesium halide as a Grignard reagent. Further, the substituted α,α-dimethylbenzyl alcohol of the formula b is halogenated by a halogenating agent to obtain the substituted α,α-dimethylbenzyl halide of the formula c. Then, the substituted α,α-dimethylbenzyl halide of the formula c thereby obtained is reacted with a cyanate, and the substituted α,α-dimethylbenzyl isocyanate of the formula d thereby formed is hydrolyzed by hydrochloric acid to obtain the substituted α,α-dimethylbenzylamine of the formula II. Here, the compound of the formula a can readily be obtained from the compound of the formula 1 by a conventional method. Further, the substituted α,α-dimethylbenzyl alcohol of the formula b can be prepared by reacting the acetophenone derivative of the formula m with a methyl magnesium halide or can also be prepared by reacting a phenyl magnesium halide of the formula o obtained from the halogenobenzene derivative of the formula n with acetone. The substituted α,α-dimethylbenzyl halide of the formula c can also be prepared by halogenating the substituted isopropylbenzene of the formula p or reacting the methylstyrene derivative of the formula q with a hydrogen halide in addition to the above-mentioned method.

Process II

The N-(substituted α,α-dimethylbenzyl)formamide of the formula e can be prepared from the substituted-α,α-dimethylbenzyl alcohol of the formula b obtained by Process I and sodium cyanide by Ritter reaction. Then, base compound is hydrolyzed by hydrochloric acid to obtain the substituted α,α-dimethylbenzylamine of the formula II in good yield.

Process III

Trimethyl silyl azide is reacted with the substituted α,α-dimethylbenzyl alcohol of the formula b obtained by Process I, and the substituted α,α-dimethylbenzyl azide of the formula f thereby obtained is reduced by a reducing agent such as sodium borohydride or Mg—CH$_3$OH, or reduced with hydrogen in the presence of a catalyst such as Pd-BaSO$_4$ or Pd-C without isolation to obtain the substituted α,α-dimethylbenzylamine of the formula II.

Process IV

The substituted benzoyl halide of the formula a is reduced by a suitable reducing agent to form the substituted benzyl alcohol of the formula g, followed by halogenating it with a halogenating agent to obtain the substituted benzyl halide of the formula h. Further, this substituted benzyl halide of the formula h can also be prepared by halogenating the compound of the formula r. Then, the substituted benzyl halide of the formula h is subjected to cyanogenation to obtain the substituted benzyl cyanide of the formula i. The substituted benzyl cyanide of the formula i is subjected to dimethylation to obtain the substituted α,α-dimethylbenzyl cyanide of the formula j. The substituted α,α-dimethylphenylacetamide of the formula k can be obtained by the hydrolysis of the compound of the formula j, and then the substituted α,α-dimethylbenzylamine of the formula II can be obtained by Hofmann reaction.

The α,α-dimethylbenzylamines thereby obtained will be exemplified in Table 2.

TABLE 2

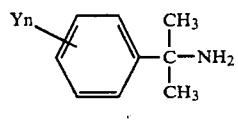

| Intermediate No. | Yn | Physical property | Melting point (°C.) or refractive index ($n_D^{20}$) |
|---|---|---|---|
| 1 | 3-CF$_3$ | Colorless liquid | Not measurable |
| 2 | 3,5-Cl$_2$ | Colorless liquid | 1.5491 |
| 3 | 3,5-(CF$_3$)$_2$ | Colorless liquid | Not measurable |
| 4 | 3,5-(OCH$_3$)$_2$ | Colorless liquid | 1.5243 |
| 5 | 3,5-Cl$_2$ 4-F | Colorless crystals | 73–75 |
| 6 | 3,4,5-Cl$_3$ | Colorless crystals | 56–59 |
| 7 | 2,4-F$_2$ 3,5-Cl$_2$ | Colorless crystals | 43–46 |
| 8 | 2,3,4,5,6-F$_5$ | Colorless liquid | 1.4468 |
| 9 | 3,5-(OCHF$_2$)$_2$ | Brown liquid | 1.4581 |
| 10 | 3,5-I$_2$ | Colorless liquid | 1.6345 |
| 11 | 3,5-Cl$_2$ 4-OCH$_3$ | Colorless liquid | 1.5460 |
| 12 | 3-Cl,4-F | Colorless liquid | 1.5162 |
| 13 | 2,3-Cl$_2$ | Colorless liquid | 1.5514 |
| 14 | 2,5-Cl$_2$ | Colorless liquid | 1.5489 |
| 15 | 4-CN | Colorless liquid | 1.5490 |
| 16 | 3-OPh | Brown liquid | 1.5728 |
| 17 | 3-SPh | Slightly yellow liquid | 1.6134 |
| 18 | 3-SCH$_3$ | Yellow liquid | 1.5707 |
| 19 | 3-Cl,5-OPh | Colorless liquid | 1.5720 |
| 20 | 3,5-F$_2$ | Colorless liquid | 1.4820 |
| 21 | 3-Br; 5-OPh | Colorless liquid | 1.5897 |
| 22 | 3-Cl; 4-OPh | Yellow liquid | 1.5771 |
| 23 | 4-OPh | Colorless liquid | 1.5667 |
| 24 | 3,5-Cl$_2$; 4-SCH$_3$ | Slightly yellow liquid | 1.5832 |
| 25 | 4-NO$_2$ | Brown liquid | Not measurable |
| 26 | 3-Cl; 4-OCH$_3$ | Colorless liquid | Not measurable |
| 27 | 3-Cl; 5-OCH$_3$ | Colorless liquid | 1.5341 |

Note:
Ph: Phenyl (2) Process for producing the compound of the present invention wherein in the formula I, R is a hydrogen atom

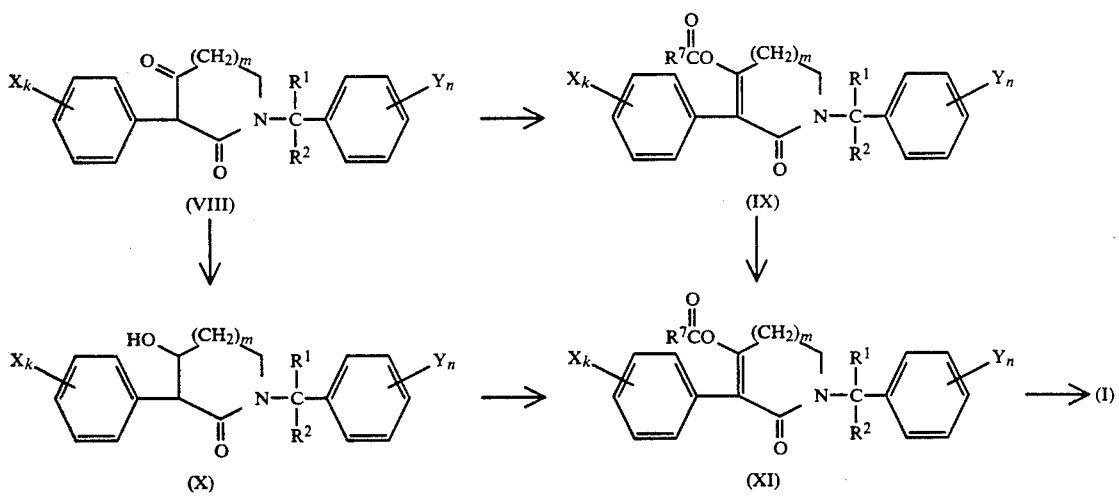

In the formulas, $R^7$ is an alkyl group or a phenyl group, and $R^1$, $R^2$, X, Y, m, k and n are as defined above.

The intermediate of the formula VIII is acylated by a suitable acylating agent without a solvent or in a suitable solvent to obtain intermediate of the formula IX. The reaction successfully proceeds in the presence of a base. Further, the reaction is conducted optionally under heating or cooling, preferably at a temperature of from 0° to 50° C. After completion of the reaction, the intermediate of the formula IX can be isolated from the reaction mixture by a usual method. For example, ice water is added to the reaction mixture, and the mixture is extracted with a water-immicible solvent, washed with water, and the solvent is distilled off to obtain the intermediate of the formula IX in good yield. The acylating agent includes acid halides such as acetyl chloride, propionyl chloride and benzoyl chloride, and acid anhydrides such as acetic anhydride, propionic anhydride and benzoic anhydride. The solvent includes hydrocarbons such as benzene, toluene and xylene, ethers such as diethyl ether, dioxane, tetrahydrofuran and dimethoxyethane, halogenated hydrocarbons such as methylene chloride and chloroform, acetone, acetonitrile and pyridine. The base includes inorganic bases such as sodium hydroxide, potassium hydroxide, sodium carbonate and potassium carbonate, and organic amines such as triethylamine, pyridine and DBU. Then, the intermediate of the formula IX is hydrogenated in a suitable solvent in the presence of a suitable catalyst under an atmospheric pressure or optionally under an elevated pressure, at room temperature, optionally under heating to obtain the intermediate of the formula XI. After completion of the reaction, the catalyst is removed by filtration, and the solvent is distilled off to isolate the intermediate of the formula XI. If necessary, the intermediate of the formula XI may be purified by recrystallization, column chromatography or the like. The catalyst includes Pd-BaSO$_4$, platinum oxide, Pd-C and the like. The solvent includes ethyl alcohol, methyl alcohol, acetone and the like.

Further, when m is 1, the intermediate of the formula XI can also be prepared from the intermediate of the formula VIII via the intermediate of the formula X by the following process.

Namely, the intermediate of the formula VIII is dissolved in an organic solvent and reacted by an addition of a suitable reducing agent to obtain the intermediate of the formula X. The temperature is within a range of from room temperature to the boiling point of the solvent. After completion of the reaction, the intermediate of the formula X can be isolated by a usual method. For example, the reaction mixture is poured into water, or water is added to the reaction mixture after distillation of the solvent. When crystals are precipitated, the crystals are isolated by filtration to obtain the intermediate of the formula X. When crystals are not precipitated, the extraction is conducted with a water-immicible solvent, followed by distillation of the solvent to obtain the intermediate of the formula X in good yield. If necessary, it may be purified by recrystallization, distillation, column chromatography or the like. The organic solvent includes hydrocarbons such as benzene, toluene and xylene, alcohols such as ethyl alcohol and methyl alcohol, ethers such as diethyl ether, dioxane, tetrahydrofuran and dimethoxyethane, and aprotic polar solvents such as N,N-dimethylformamide and N,N-dimethylacetamide. The reducing agent includes sodium metal, ammonium lithium, sodium amalgam, zinc metal, aluminum metal, tributyltin hydride, lithium aluminum hydride, aluminum tri-tert-butoxy lithium hydride, sodium borohydride and lithium borohydrocyanide. Then, the intermediate of the formula X thereby obtained is dissolved in a suitable organic solvent and reacting by an addition of suitable acylating agent and a base to obtain the intermediate of the formula XI. The reaction is conducted added at room temperature or optionally under heating or cooling, preferably at a temperature within a range of from 0° C. to the boiling point of the solvent. After completion of the reaction, the intermediate of the formula XI can be isolated by a usual method. For example, the reaction mixture is poured into water, extracted with a water-immicible solvent and concentrated after washing with water to isolate the intermediate of the formula XI. If necessary, it may be purified by recrystallization, distillation, column chromatography or the like. The acylating agent includes acid halides such as acetic acid chloride, propionic acid chloride and benzoic acid chloride, and acid anhydrides such as acetic anhydride, propionic anhydride and benzoic anhydride. The base includes inorganic bases such as sodium hydroxide, potassium hydroxide and sodium carbonate, metal alcoholates such as sodium methylate, sodium ethylate and potassium tert-butoxide, and organic amines such as pyridine and triethylamine. The organic solvent includes hydrocarbons such as benzene, toluene and xylene, halogenated hydrocarbons such as chloroform, methylene chloride and chlorobenzene, ethers such as diethyl ether, dioxane, tetrahydrofuran and dimethoxyethane, acetone, aprotic polar solvents such as acetonitrile, N,N-dimethylformamide, N,N-dimethylacetamide and pyridine.

The intermediate of the formula XI obtained by the above two methods is reacted in a suitable solvent in the presence of a base to obtain the compound of the present invention wherein in the formula I, R is a hydrogen atom. The reaction is conducted at a temperature not lower than room temperature, preferably at from room temperature to the boiling point of the solvent. After completion of the reaction, the desired compound can be isolated from the reaction mixture by a usual method. For example, the reaction mixture is washed with water, and then the solvent is distilled off, or the reaction mixture is poured into water and extracted with a suitable solvent, and the extract is washed with water and concentrated to obtain the desired compound. The base includes inorganic bases such as sodium hydroxide, potassium hydroxide, sodium carbonate and potassium carbonate and organic amines such as triethylamine, pyridine and DBU. The solvent includes hydrocarbons such as benzene, toluene and xylene, alcohols such as ethyl alcohol and methyl alcohol, ethers such as dioxane, tetrahydrofuran and dimethoxyethane, and aprotic polar solvents such as N,N-dimethylformamide, N,N dimethylacetamide, pyridine and acetonitrile.

Next the process for producing the intermediate of the formula VIII which is used as the starting material for the production of the compound of the present invention wherein R is a hydrogen atom, will be mentioned.

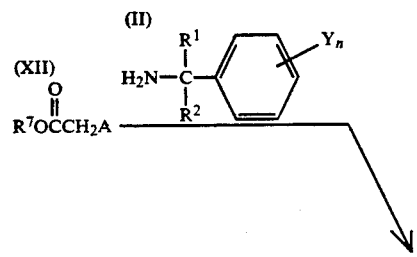

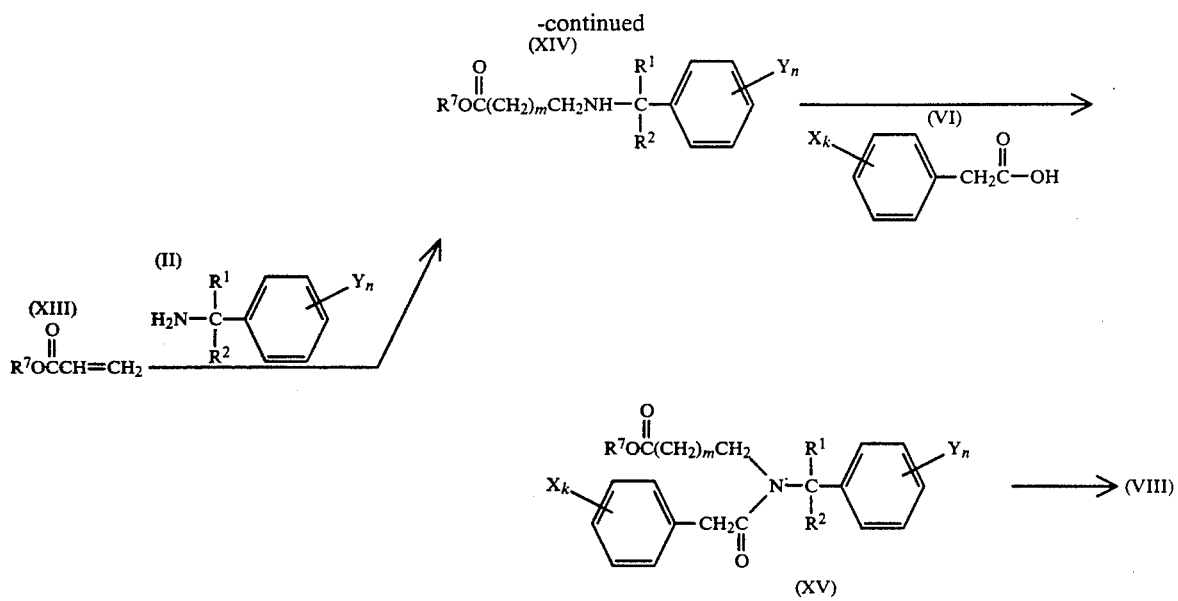

In the above formulas, $R^1$, $R^2$, $R^7$, X, Y, A, m, k and n are as defined above.

When m is 0, the intermediate of the formula XIV can be obtained in good yield by reacting the benzylamine of the formula II with the halogenated acetate derivative of the formula XII without a solvent or in a suitable solvent. The reaction successfully proceeds in an organic solvent in the presence of a base. The reaction is conducted at room temperature, optionally under heating or cooling, preferably at a temperature within a range of from 0° C. to the boiling point of the solvent. After completion of the reaction, the intermediate of the formula XIV can be isolated from the reaction mixture by a usual method. For example, the reaction mixture is washed with water, followed by distillation of the solvent, or the reaction mixture is poured into water, extracted with a water-immicible solvent, followed by distillation of the solvent to obtain the intermediate of the formula XIV. Further, if necessary, it may be purified distillation, column chromatography or the like. The solvent to be used in the reaction, includes hydrocarbons such as benzene, toluene and xylene, alcohols such as ethyl alcohol and methyl alcohol, ethers such as diethyl ether, dioxane, tetrahydrofuran and dimethoxyethane, halogenated-hydrocarbons such as methylene chloride and chloroform, ketones such as acetone and methyl ethyl ketone, and aprotic polar solvents such as acetonitrile, N,N-dimethylformamide, N,N-dimethylacetamide and dimethylsulfoxide. The base to be used includes organic amines such as triethylamine, pyridine, N,N-dimethylaniline, N-methylmorphorine and quinoline, inorganic bases such as sodium hydroxide, potassium hydroxide, sodium carbonate and potassium carbonate, metal alcoholates such as sodium methylate and sodium ethylate, and sodium hydride.

Further, when m is 1, the intermediate of the formula XIV can be prepared by reacting the benzylamine of the formula II with the acrylate derivative of the formula XIII. The reaction of this method is conducted without a solvent or in a suitable solvent under a nitrogen stream. Further, if necessary, a suitable catalyst is employed. The reaction is conducted at a temperature not lower than room temperature, preferably at from 50° to 150° C. After completion of the reaction, the intermediate of the formula XIV can be isolated by a usual method. For example, compounds having low boiling points are distilled off under reduced pressure, or the reaction mixture is washed with water, followed by distillation of the solvent to obtain the intermediate of the formula XIV. If necessary, it may be purified by distillation, column chromatography or the like. The solvent includes hydrocarbons such as benzene, toluene and xylene, alcohols such as ethyl alcohol and methyl alcohol, ethers such as diethyl ether, dioxane, tetrahydrofuran and dimethoxy ethane and halogenated hydrocarbons such as methyl chloride and chloroform. The catalyst includes organic amines such as triethylamine and pyridine, metal alcoholates such as sodium methylate and sodium ethylate, and inorganic bases such as potassium carbonate and sodium carbonate.

Then, the compound of the formula XIV is dissolved in a suitable organic solvent and reacted with a reactive derivative of the substituted-phenyl acetic acid of the formula VI to obtain the intermediate of the formula XV in good yield. The reaction is conducted at room temperature or optionally under heating or cooling, preferably at a temperature within a range of from 0° C. to the boiling point of the solvent. Further, the reaction successfully proceeds in the presence of a base. The base may be added as it is or as an aqueous solution. After completion of the reaction, the intermediate of the formula XV can be isolated from the reaction mixture by a usual method. For example, water is added to the reaction mixture, and the mixture is washed with water, followed by distillation of the solvent, or the reaction mixture is poured into water, extracted with a water-immicible solvent, followed by distillation of the solvent to obtain the intermediate of the formula XV. If necessary, it may be purified by recrystallization, distillation, column chromatography or the like. The organic solvent includes hydrocarbons such as benzene, toluene and xylene, ethers such as diethyl ether, dioxane, tetrahydrofuran and dimethoxyethane, halogenated hydrocarbons such as methylene chloride and chloroform, ketones such as acetone and methyl ethyl ketone, and aprotic polar solvents such as acetonitrile, N,N-dimethylformamide and N,N-dimethylacetamide. The reactive derivative of the substituted-phenyl acetic acid includes the acid anhydride, acid chloride, acid bromide and active esters thereof which can readily be prepared from the substituted-phenyl acetic acid by a conventional method. The base includes organic amines such as triethylamine, pyridine, N,N-dimethylaniline, N-methylmorphorine and quinoline, and inorganic bases such as sodium hydroxide, potassium hydroxide, sodium carbonate and potassium carbonate.

The intermediate of the formula XV thereby obtained is subjected to ring closure without a solvent or in a suitable solvent in the presence of a reaction assistant to obtain the intermediate of the formula VIII. The reaction is conducted at a temperature not lower than room temperature, preferably at a temperature within a range of from room temperature to the boiling point of the solvent. After completion of the reaction, the intermediate of the formula VIII can be isolated from the reaction mixture by a usual method. For example, the solvent is distilled off, and the residue is poured into ice water and acidified with hydrochloric acid to precipitate the intermediate of the formula VIII. The precipitated intermediate of the formula VIII is collected by filtration and washed with water, or the residue is extracted by a suitable water-immicible organic solvent, washed with water and concentrated to isolate the intermediate of the formula VIII. If necessary, it may be purified by recrystallization, column chromatography or the like. The solvent includes hydrocarbons such as benzene, toluene and xylene, alcohols such as methyl alcohol and ethyl alcohol, ethers such as dioxane, tetrahydrofuran and dimethoxyethane and aprotic polar solvents such as acetonitrile, N,N-dimethylformamide and N,N-dimethylacetamide. The reaction assistant includes metal hydrides such as sodium hydride, metal alcoholates such as sodium ethylate, sodium methylate and potassium tert-butoxide, and inorganic bases such as sodium hydroxide and potassium hydroxide.

(3) Process for the production of the compound of the present invention wherein in the formula I, Y is a hydroxyl group

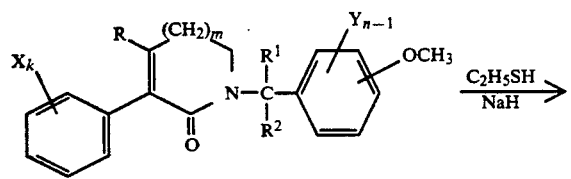

(XVI)

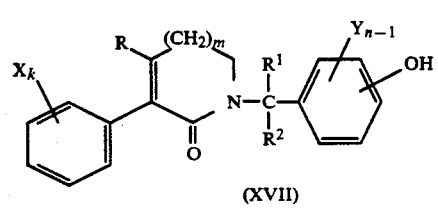

(XVII)

In the formulas, R, $R^1$, $R^2$, X, Y, m, k and n are as defined above.

The compound of the formula XVII can be prepared by reacting the compound of the formula XVI with a dealkylating agent in an organic solvent in the presence of a base. The reaction is conducted at a temperature within a range of from 0° C. to the boiling point of the solvent. After completion of the reaction, the reaction solution is poured into ice water, extracted with a water-immicible organic solvent after acidification and concentrated to isolate the compound of the formula XVII. If necessary, it may be purified by recrystallization, column chromatography or the like. As the dealkylating agent, ethylmercaptan may be used. As the base, sodium hydride may be used. The reaction solvent includes aprotic polar solvents such as dimethylformamide and dimethylacetamide.

(4) Process for the production of the present invention wherein in the formula I, Y is an alkoxy group, a cycloalkoxy group, an alkenyloxy group, an alkynyloxy group, a benzyloxy group, a phenoxy group, a haloalkoxy group, an alkoxyalkoxy group, an alkoxycarbonylalkoxy group or a cyanoalkoxy group

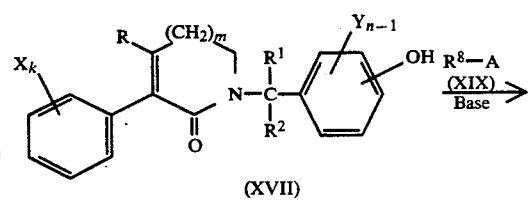

(XVII)

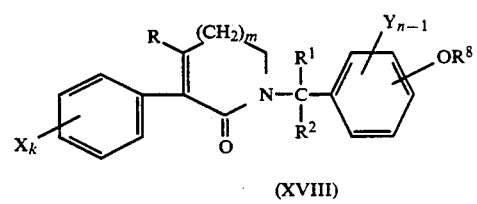

(XVIII)

In the above formulas, $R^8$ is an alkyl group, a cycloalkyl group, an alkenyl group, an alkynyl group, a benzyl group, a phenyl group, a haloalkyl group, an alkoxyalkyl group or an alkoxy carbonylalkyl group, and R, $R^1$, $R^2$, X, Y, A, m, k and n are as defined above.

The compound of the formula XVIII can be prepared by reacting the compound of the formula XVII obtained in process (3) with a various alkylating agents of the formula XIX in the presence of a base in a suitable solvent. The reaction is conducted at a temperature within a range of from room temperature to the boiling point of the solvent. After completion of the reaction, the reaction mixture is poured into a large amount of water, extracted with a water-immicible solvent and concentrated to obtain the compound of the formula XVIII. If necessary, it may be purified by recrystallization or column chromatography. The base includes inorganic bases such as sodium carbonate, potassium carbonate, sodium hydroxide and potassium hydroxide, and organic amines such as triethylamine and pyridine. The reaction solvent includes alcohols such as methyl alcohol and ethyl alcohol, and aprotic polar solvents such as acetonitrile, dimethylformamide and dimethyl acetamide.

(5) Process for the production of the compound of the present invention wherein in the formula I, Y is an alkylsulfonyl group or a phenylsulfonyl group

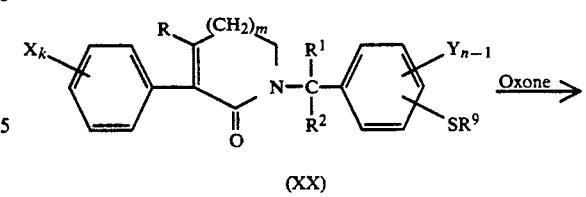

(XX)

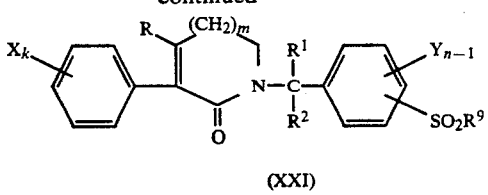

(XXI)

In the formulas, $R^9$ is alkyl group, and R, $R^1$, $R^2$, X, Y, A, m, k and n are as defined above.

The compound of the formula XXI can be prepared by oxidizing the compound of the formula XX in a suitable solvent. The reaction is successfully conducted at a temperature within a range of from 0° to 50° C. After completion of the reaction, the reaction solution is poured into ice water, followed by filtration or extraction to isolate the compound of the formula XXI. As the oxidizing agent, Oxone may be used. As the reaction solvent, a solvent mixture of methanol/water may be used.

Now, the processes for the production of the compounds of the present invention and the intermediates thereof will be described in further detail with reference to Reference Examples and Examples, However, it should be understood that the present invention is by no means restricted such specific Examples.

REFERENCE EXAMPLE 1

Preparation of 3,5-dichloro-α,α-dimethylbenzylamine 100 ml of an aqueous solution of 18.0 g of (0.45 mol) of sodium hydroxide was cooled with ice water, and 14.4 g (0.09 mol) of bromine was gradually dropwise added thereto at 0° C. After completion of the dropwise addition, the solution was returned to room temperature and stirred for 0.5 hour. Then, 20.9 g (0.09 mol) of 3,5-dichloro-α,α-dimethylphenylacetamide was added thereto at once. The mixture was cooled, and the stirring was continued for one hour. Then, the reaction mixture was heated at 80° C. and reacted for one hour. The reaction solution was returned to room temperature, then extracted with diethyl ether and dried over anhydrous magnesium sulfate. The solvent was distilled off to obtain 11.2 g (yield: 61.1%) of the desired compound as colorless liquid.

Refractive index: 1.5491

$^1$H-NMR(CDCl$_3$, δ) 1.44(s, 6H), 1.30–1.74(br, 2H), 7.10–7.50(m, 3H)

REFERENCE EXAMPLE 2

Preparation of 3,5-dichloro-α,α-dimethylbenzylamine

To 7 ml of acetic acid, 2.83 g (57.8 mmol) of sodium cyanide was gradually added at a temperature not higher than 20° C. To the suspension thereby obtained, 7 ml of an acetic acid solution of 7 ml of concentrated sulfuric acid was dropwise added at not higher than 20° C., and the mixture was stirred at room temperature for one hour. Then, 10.3 g (50 mmol) of 3,5-dichloro-α,α-dimethylbenzyl alcohol was dropwise added thereto at not higher than 20° C. The reaction mixture was stirred at room temperature for two days, and then poured into ice water. The mixture was alkalified with potassium carbonate and extracted with ethyl acetate. The ethyl acetate solution was washed with water, dried and then concentrated. The solid thereby obtained was washed with n-hexane and collected by filtration to obtain 8.2 g (yield: 70.7%) of N-(3,5-dichloro-α,α-dimethylbenzyl)-formamide as white needle-like crystals.

Melting point: 115°–117° C.

A mixture of 1.16 g (5 mmol) of N-(3,5-dichloroα,α-dimethylbenzyl)formamide and 8 ml of 2N hydrochloric acid was refluxed for 30 minutes. After cooling, the reaction solution was alkalified with a sodium hydroxide aqueous solution and extracted with diethyl ether. The ether solution was washed with water, dried and then concentrated to obtain 1.0 g (yield: 98.0%) of the desired compound.

REFERENCE EXAMPLE 3

Preparation of 3,4,5-trichloro-α,α-dimethylbenzylamine 100 g (0.388 mmol) of 3,4,5-trichloro-α,α-dimethylbenzyl chloride was dissolved in 500 ml of toluene, and 76 g (0.507 mol) of silver cyanate was added thereto. The mixture was stirred at 80° C. on a hot water bath for one hour. After completion of the reaction, insolubles were removed by filtration, and toluene was distilled off to obtain 3,4,5-trichloro-α,α-dimethylbenzyl isocyanate. This compound is gradually dropwise added to 1.5 l of 8N hydrochloric acid at from 60° to 65° C. under stirring by a mechanical stirrer. The mixture was stirred at from 60° to 65° C. for 2 hours and then stirred at room temperature over night. Precipitated hydrochloride of the amine was collected by filtration and washed with toluene. Further, the filtrate was washed with toluene. Then, the aqueous layer and the hydrochloride collected by filtration were mixed, and the mixture was alkalified with a sodium hydroxide aqueous solution and extracted with diethyl ether. The ether layer was washed with water, dried and then subjected to distillation to obtain 37.8 g (yield: 41%) of the desired compound as white crystals.

Melting point: 56°–59° C.

$^1$H-NMR(CDCl$_3$, δ) 1.43(s, 6H), 1.40–1.66(br, 2H), 7.50(s, 2H)

REFERENCE EXAMPLE 4

Preparation of 3,5-dichloro-4-methoxy-α,α-dimethylbenzylamine

A benzene solution of 23.6 g (0.1 mol) of 3,5-dichloro-4-methoxy-α,α-dimethylbenzyl alcohol and 13.9 g (0.12 mol) of trimethylsilyl azide were cooled with ice water, and 17.1 g (0.12 mol) of boron trifluoride ethyl etherate was dropwise added thereto at a temperature not higher than 20° C. under stirring. After completion of the dropwise addition, the mixture was stirred for one hour as it was and further at room temperature for 4 hours. The reaction solution was poured into ice water, and the organic layer was washed with a saturated sodium hydrogencarbonate aqueous solution and with water. To this benzene solution, 5.1 g (0.01 mol) of n-hexadecyl tri-n-butylphosphonium bromide was added, and an aqueous solution of 32.4 g (0.9 mol) of sodium borohydride was dropwise added thereto at 80° C. in three times. The reaction solution was poured into water. The organic layer was washed with water and then subjected to liquid separation by an addition of concentrated hydrochloric acid. The aqueous layer was alkalified with sodium hydroxide and then extracted with diethyl ether. The ether solution was dried over anhydrous magnesium sulfate, and the solvent was distilled off under reduced pressure to obtain 14.9 g of the desired compound.

Refractive index: 1.5460

$^1$H-NMR(CDCl$_3$, δ) 1.45 (s,6H), 1.50 (s,2H), 3.86 (s,3H), 7.40 (s,2H)

REFERENCE EXAMPLE 5

Preparation of 1-(3-chloro-α,α-dimethylbenzylamino)-2-propanone 27.8 g (0.3 mol) of chloroacetone, 16.0 g (0.1 mol) of 3-chloro-α,α-dimethylbenzylamine and 11.2 g (0.11 mol) of triethylamine were dissolved in 200 ml of N,N-dimethylacetamide, and the mixture was heated at 80° C. for 3 hours under stirring. The reaction solution was cooled, then poured into a large amount of water and extracted with toluene. The toluene layer was washed with water and then dried over anhydrous magensium sulfate. Then, the toluene layer was distilled off under reduced pressure to obtain 6.9 g (yield: 30.6%) of the desired compound.

Boiling point: 100°-105° C./0.05 mmHg $^1$H-NMR(CDCl$_3$, δ) 1.43(s, 6H), 2.06(s, 3H), 2.33(s, 1H), 3.30(s, 2H), 7.32(m, 4H)

REFERENCE EXAMPLE 6

Preparation of N-(3-chloro-α,α-dimethylbenzyl)-N-(2-oxopropyl)-phenylacetamide 22.6 g (0.1 mol) of 1-(3-chloro-α,α-dimethylbenzylamino)-2-propanone prepared by the method of Reference Example 5, was dissolved in 200 ml of acetone, and 14.0 g (0.11 mol) of potassium carbonate was added thereto. The mixture was cooled with ice water, and then 15.5 g (0.1 mol) of phenylacetyl chloride was gradually dropwise added thereto under stirring. After completion of the dropwise addition, the reaction mixture was returned to room temperature and stirred for 3 hours. Then, the solvent was distilled off under reduced pressure, and then water was added to the residue, and the mixture was extracted with ethyl acetate. The ethyl acetate layer was dried over anhydrous magnesium sulfate, and the solvent was distilled off under reduced pressure. The residue was crystallized from n-hexane to obtain 21.5 g (yield: 62.5%) of the desired compound.

Melting point: 98°-100° C.

$^1$H-NMR (CDCl$_3$, δ) 1.65(s, 6H), 2.18(s, 3H), 3.32(s, 2H), 4.31(s, 2H), 7.32(m, 9H)

EXAMPLE 1

Preparation of 1-(3-chloro-α,α-dimethylbenzyl)-4-methyl-3-phenyl-3-pyrrolin-2-one (Compound No. 88)

34.4 g (0.1 mol) of N-(3-chloro-α,α-dimethylbenzyl)-N-(2-oxopropyl)phenylacetamide prepared in accordance with the method of Reference Example 6, was dissolved in 200 ml of ethanol, and 0.5 (0.009 mol) of sodium hydroxide powder was added thereto. The mixture was refluxed under heating for 10 minutes. Then, the solvent was distilled off under reduced pressure, and then water was added thereto. The mixture was extracted with ethyl acetate. The ethyl acetate layer was dried over anhydrous magnesium sulfate, and then the solvent was distilled off under reduced pressure, followed by purification by silica gel column chromatography (n-hexane/ethyl acetate) to obtain 21.2 g (yield: 65.2%) of the desired compound.

Melting point: 102°-103° C.

$^1$H-NMR (CDCl$_3$, δ) 1.76(s, 6H), 2.10(s, 3H), 3.90(s, 2H), 7.26(m, 9H)

REFERENCE EXAMPLE 7

Preparation of 1-(3,5-dichloro-4-methoxy-α,α-dimethylbenzylamino)-2-propanone 10.0 g (0.1 mol) of chloroacetone, 14.1 g (0.06 mol) of 3,5-dichloro-4-methoxy-α,α-dimethylbenzylamine and 7.2 g (0.07 mol) of triethylamine were dissolved in 100 ml of N,N-dimethylacetamide, and the mixture was heated at 80° C. for about three hours under stirring under a nitrogen atmosphere. The reaction solution was cooled, then poured into a large amount of water and extracted with ethyl acetate. The ethyl acetate layer was washed with water and then dried over anhydrous magensium sulfate. The solvent was distilled off under reduced pressure to obtain 9.5 g (yield: 89%) of the desired compound.

Refractive index: 1.5315

$^1$H-NMR(CDCl$_3$, δ) 1.42(s, 6H), 2.11(s, 3H), 2.27(s 1H), 3.30(s, 2H), 3.89(s, 3H), 7.33(s, 2H)

REFERENCE EXAMPLE 8

Preparation of N-(3,5-dichloro-4-methoxy-α,α-dimethylbenzyl)-N-(2-oxopropyl)phenylacetamide 8.8 g (0.03 mol) of 1-(3,5-dichloro-4-methoxy-α,α-dimethylbenzylamino)-2-propane prepared by the method of Reference Example 7, was dissolved in 40 ml of acetone and 4.6 g (0.033 mol) of potassium carbonate was added thereto. 5.2 g (0.033 mol) of phenylacetyl chloride was gradually dropwise added thereto under cooling with ice and stirring. After completion of the dropwise addition, the reaction mixture was returned to room temperature and stirred for 3 hours. Then, the solvent was distilled off under reduced pressure. Water was added to the residue and extracted with ethyl acetate. The ethyl acetate layer was dried over anhydrous magnesium sulfate, and then the solvent was distilled off under reduced pressure. The residue was crystallized from n-hexane to obtain 10.2 g (yield: 83%) of the desired compound as colorless crystals.

Melting point: 126°-127° C.

$^1$H-NMR(CDCl$_3$, δ) 1.60(s, 6H), 2.20(s, 3H), 3.45(s, 2H), 4.24(s, 2H), 3.93(s, 3H), 7.27(s, 2H), 7.62(m, 5H)

EXAMPLE 2

Preparation of 1-(3,5-dichloro-4-methoxy-α,α-dimethylbenzyl)-4-methyl-3-phenyl-3-pyrrolin-2-one (Compound No. 143)

0.5 g (0.008 mol) of potassium hydroxide powder was added to an ethyl alcohol solution of 8.2 g (0.02 mol) of N-(3,5-dichloro-4-methoxy-α,α-dimethylbenzyl)-N-(2-oxopropyl)phenylacetamide prepared by the method of Reference Example 8, and the mixture was refluxed under heating for 20 minutes. The reaction solution was cooled, and then ethanol was distilled off under reduced pressure. Water was added to the residue and extracted with ethyl acetate. The ethyl acetate layer was dried over anhydrous magnesium sulfate, and then the solvent was distilled off under reduced pressure, followed by purification by silica gel column chromatography to obtain 5.2 g (yield: 66%) of the desired compound as colorless crystals.

Melting point: 136°-139° C.

$^1$H-NMR(CDCl$_3$, δ) 1.68(s, 6H), 2.17(s, 3H), 3.87(s, 3H), 4.00(s, 2H), 7.29(s, 2H), 7.52(m, 5H)

EXAMPLE 3

Preparation of
1-(3,5-dichloro-α,α-dimethylbenzyl)-3-(2-fluorophenyl)-4-methyl-3-pyrrolin-2-one (Compound No. 134)

6.8 g (17 mmol) of N-(3,5-dichloro-α,α-dimethylbenzyl)-N-(2-oxopropyl)-2-fluorophenylacetamide (having a melting point of from 167° to 170° C.) prepared in accordance with the method of Reference Example 8, was dissolved in 30 ml of ethanol, and 0.7 g (11 mmol) of sodium hydroxide powder was added thereto. The mixture was refluxed under heating for 10 minutes. The reaction solution was cooled, and then ethanol was distilled off under reduced pressure. Water was added to the residue and extracted with ethyl acetate. The ethyl acetate layer was dried over anhydrous magnesium sulfate, and then the solvent was distilled off under reduced pressure. The crude crystals thereby obtained was recrystallized from methanol to obtain 3.1 g (yield: 49%) of the desired compound as colorless crystals.

Melting point: 177°–180° C.

$^1$H-NMR(CDCl$_3$, δ) 1.83(s, 6H), 2.10(d, 3H), 4.13(s, 2H), 7.30(m, 7H)

EXAMPLE 4

Preparation of
4-methyl-3-phenyl-1-(3,4,5-trichloro-α,α-dimethylbenzyl)-3-pyrrolin-2-one (Compound No. 113)

40 g (96.9 mmol) of N-(2oxopropyl)-N-(3,4,5-trichloro-α,α-dimethylbenzyl)phenylacetamide (having a melting point of from 149° to 153° C.) prepared in accordance with the method of Reference Example 8, was dissolved in 500 ml of ethanol under heating, and 3.2 g (48.5 mmol) of potassium hydroxide powder was added thereto. The mixture was refluxed under heating for 10 minutes. The reaction solution was cooled, and then precipitated crystals were collected by filtration, washed with water and then air-dried. The filtrate was distilled under reduced pressure to remove the solvent, and then water was added thereto and extracted with ethyl acetate. The extract was washed with water and then dried over anhydrous magensium sulfate. The solvent was distilled off under reduced pressure to obtain crude crystals. This crude crystals and the crystals previously collected by filtration were put together and recrystallized from ethyl acetate to obtain 33.7 g (yield: 88.1%) of the desired compound as colorless crystals.

Melting point: 181°–183° C.

$^1$H-NMR(CDCl$_3$, δ) 1.73(s, 6H), 2.16(s, 3H), 4.03(s, 2H), 7.10–7.78(m, 7H)

EXAMPLE 5

Preparation of
1-(3,5-dichloro-4-fluoro-α,α-dimethylbenzyl)-4-methyl-3-phenyl-3-pyrrolin-2-one (Compound No. 114)

4.0 g (0.01 mol) of N-(3,5-dichloro-4-fluoro-α,α-dimethylbenzyl)-N-(2-oxopropyl)phenylacetamide prepared in accordance with the method of Reference Example 8, was dissolved in 50 ml of ethyl alcohol, and 0.5 g (0.009 mol) of potassium hydroxide powder was added thereto. The mixture was refluxed under heating for 10 minutes. Then, the solvent was distilled off under reduced pressure, and water was added thereto and extracted with ethyl acetate. The ethyl acetate layer was dried over an hydrous magnesium sulfate, and then the solvent was distilled off under reduced pressure, followed by purification by silica gal column chromatography (n-hexane/ethyl acetate) to obtain 2.5 g (yield: 67.5%) of the desired compound as colorless crystals.

Melting point: 164°–167° C.

$^1$H-NMR(CDCl$_3$, δ) 1.73(s, 6H), 2.12(s, 3H), 3.98(s, 2H), 7.26(m, 7H)

REFERENCE EXAMPLE 9

Preparation of
4-(α,α-dimethylbenzylamine)-2-butanone 27.0 g (0.2 mol) of α,α-dimethylbenzylamine was added to 14.0 g (0.2 mol) of methyl vinyl ketone, and the mixture was stirred at room temperature for two days under a nitrogen atmosphere. After completion of the reaction, compounds having a low boiling point were removed by distillation under reduced pressure to obtain 38.2 g (yield: 93.9%) of the desired compound.

Boiling point: 95°–105° C./0.08 mHg $^1$H-NMR(CDCl$_3$, δ) 1.43(s, 6H), 1.77(br, 1H), 2.04(s, 3H), 2.53(s, 4H), 7.33(m, 5H)

REFERENCE EXAMPLE 10

Preparation of
(N-(α,α-dimethylbenzyl)-N-(3-oxobutyl)phenylacetamide 6.0 g (0.029 mol) of 4-(α,α-dimethylbenzylamimo)-2-butanone prepared by the method of Reference Example 9, was dissolved in 50 ml of acetone, and 4.8 g (0.035 mol) of potassium carbonate was added thereto. 5.4 g (0.035 mol) of phenyl acetic acid chloride was dropwise added thereto under stirring at room temperature. After completion of the dropwise addition, the reaction solution was stirred for one day and night. After completion of the reaction, the reaction solution was poured into water and extracted with ethyl acetate. The ethyl acetate layer was washed with water and then dried over anhydrous magnesium sulfate. The solvent was distilled off under reduced pressure, followed by purification by silica gel column chromatography (n-hexane/ethyl acetate) to obtain 7.0 g (yield: 74.5%) of the desired compound.

Refractive index: 1.5571

$^1$H-NMR(CDCl$_3$, δ) 1.70(s, 6H), 2.08(s, 3H), 2.70(m, 2H), 3.47(s, 2H), 3.87(m, 2H), 7.17(m, 10H)

EXAMPLE 6

Preparation of
1-(α,α-dimethylbenzyl)-4-methyl-3-phenyl-1,2,5,6-tetrahydropyridin-2-one (Compound No. 7)

7.1 g (0.022 mol) of N-(α,α-dimethylbenzyl)-N-(3-oxobutyl)phenylacetamide prepared by the method of Reference Example 10, was dissolved in 50 ml of ethanol, and 0.33 g (0.005 mol) of potassium hydroxide powder was added thereto. The mixture was reflux under heating for 1.5 hours. Then, the reaction mixture was returned to room temperature, and ethanol was distilled off under reduced pressure. Water was added to the residue, and the mixture was extracted with ethyl acetate. Then ethyl acetate layer was washed with water and then dried over anhydrous magnesium sulfate. The solvent was distilled off under reduced pressure. The residue thereby obtained was recrystallized from ethanol to obtain 4.5 g (yield: 67.2%) of the desired compound.

Melting point: 108°-109° C.

$^1$H-NMR(CDCl$_3$, δ) 1.73(br, 9H), 2.30(t, 2H), 3.33(t, 2H), 7.20(m, 10H)

EXAMPLE 7

Preparation of 1-(3-chloro-α,α-dimethylbenzyl)-4-methyl-3-phenyl-1,2,5,6-tetrahydropyridin-2-one (Compound No. 9)

15.0 g (0.042 mol) of N-(3-chloro-α,α-dimethylbenzyl)-N-(3-oxobutyl)phenylacetamide prepared in accordance with the method of Reference Example 10, was dissolved in 100 ml of ethanol, and 1.3 g (0.02 mol) of potassium hydroxide powder was added thereto. The mixture was refluxed under heating for three hours. After completion of the reaction, ethanol as distilled off under reduced pressure, and then ice water was added to the residue and extracted with ethyl acetate. The ethyl acetate layer was washed with water and then dried over anhydrous magnesium sulfate. The solvent was distilled off under reduced pressure. The residue thereby obtained was purified by chromatography by using a column packed with silica gel (n-hexane/ethyl acetate) to obtain 6.8 g (yield: 48.1%) of the desired compound.

Melting point: 117°-118° C.

$^1$H-NMR(CDCl$_3$, δ) 1.70(s, 6H), 1.75(s, 3H), 2.42(t, 2H), 3.47(t, 2H), 7.13(m, 9H)

EXAMPLE 8

Preparation 1-(3,5-dichloro-4-fluoro-α,α-dimethylbenzyl)-4-methyl-3-phenyl-1,2,5,6-tetrahydropyridin-2-one (Compound No. 84)

2.5 g (0.006 mol) of N-(3,5-dichloro-4-fluoro-α,α-dimethylbenzylamino)-N-(3-oxobutyl)phenylacetamide prepared in accordance with the method of Reference Example 10 was dissolved in 50 ml of ethyl alcohol, and 0.5 g (0.009 mol) of potassium hydroxide powder was added thereto. The mixture was refluxed under heating for 10 minutes. Then, the solvent was distilled off under reduced pressure, and water was added thereto and extracted with ethyl acetate. The ethyl acetate layer was dried over anhydrous magnesium sulfate, and then the solvent was distilled off under reduced pressure. Then, the residue was purified by silica gel column chromatography (n-hexane/ethyl acetate) to obtain 1.4 g (yield: 60.8%) of the desired compound.

Melting point: 154°-159° C.

$^1$H-NMR(CDCl$_3$, δ) 1.65(s, 6H), 1.77(s, 3H), 2.52(t, 2H), 3.56(t, 2H), 7.22(m, 7H)

REFERENCE EXAMPLE 11

Preparation of methyl 2-(α,α-dimethylbenzylamino)acetate 13.5 g (0.1 mol) of α,α-dimethylbenzylamine was dissolved in 200 ml of acetonitrile, and 15 g (0.11 mol) of potassium carbonate was added thereto. 15.3 g (0.1 mol) of methyl bromoacetate was gradually dropwise added thereto under cooling with ice. After completion of the dropwise addition, reaction mixture was returned to room temperature and stirred for one day and night. Salts were removed by filtration, and acetonitrile was distilled off under reduced pressure. Water was added to the residue and extracted with ethyl acetate. The ethyl acetate layer was thoroughly washed with water and then dried over anhydrous magnesium sulfate. The solvent was distilled off under reduced pressure, and the residue was subjected to distillation to obtain 12.1 g (yield: 60%) of the desired compound.

Boiling point: 90°-100° C./0.06 mmHg $^1$H-NMR(CDCl$_3$, δ) 1.50(s, 6H), 1.90(br, 1H), 3.16(s, 2H), 3.67(s, 3H), 7.33(m, 5H)

REFERENCE EXAMPLE 12

Preparation of methyl 2-(N-phenylacetyl-α,α-dimethylbenzylamino) acetate 12 g (59 mmol) of methyl 2-(α,α-dimethylbenzylamino) acetate prepared by the method of Reference Example 11, was dissolved in 100 ml of acetone, and 8.5 g (61 mmol) of potassium carbonate was added thereto. Then, 9.0 g (58 mmol) of phenyl acetic acid chloride dissolved in 20 ml of acetone was gradually dropwise added thereto under cooling with ice. After completion of the dropwise addition, the reaction mixture was returned room temperature and stirred for one day and night as it was. The reaction solution was poured into ice water, and precipitated crystals were collected by filtration. The crystals thereby obtained was washed with water and then dried to obtain 15 g (yield: 79%) of the desired compound.

Melting point: 99°-101° C.

$^1$H-NMR(CDCl$_3$, δ) 1.67(s, 6H), 3.33(br, 2H), 3.67(s, 3H), 4.20(br, 2H), 7.33(m, 10H)

REFERENCE EXAMPLE 13

Preparation of 1-(α,α-dimethylbenzyl)-4-hydroxy-3-phenyl-3-pyrrolin-2-one 10 g (30 mmol) of methyl 2-(N-phenylacetyl-α,α-dimethylbenzylamino)acetate was dissolved in 100 ml of ethanol, and 17.4 g (90 mmol) of a methanol solution of 28% sodium methylate was added thereto. The mixture was refluxed under heating for 0.5 hour. The reaction solvent was distilled off under reduced pressure, and the residue was poured into ice water and acidified with 10% hydrochloric acid. Precipitated crude crystals were collected by filtration and recrystallized from ethanol to obtain 4.0 g (yield: 46%) of the desired compound.

Melting point: 206°-208° C.

$^1$H-NMR(CDCl$_3$+DMSO-d$_6$, δ) 1.80(s, 6H), 3.87(s, 2H), 7.30(m, 8H), 7.90(m, 2H), 10.5(br, 1H)

REFERENCE EXAMPLE 14

Preparation of 4-acetoxy-1-(α,α-dimethylbenzyl)-3-phenyl-3-pyrrolin-2-one 5 g (17 mmol) of 1-(α,α-dimethylbenzyl)-4-hydroxy-2-oxo-3-phenyl-3-pyrroline prepared by the method of Reference Example 13, was dissolved in a solution of 10 ml of acetic anhydride and 20 ml of pyridine, and the solution was stirred at room temperature for one day and night. Ice water was added to the reaction solution and extracted with ethyl acetate. The ethyl acetate layer was thoroughly washed with water and then dried over anhydrous magnesium sulfate. The solvent was distilled off under reduced pressure, and the residue was recrystallized from isopropyl ether to obtain 4.2 g (yield: 81%) of the desired compound.

Melting point: 149°-150° C.

$^1$H-NMR(CDCl$_3$, δ) 1.87(s, 6H), 2.23(s, 3H), 4.33(s, 2H), 7.33(m, 8H), 7.77(m, 2H)

REFERENCE EXAMPLE 15

Preparation of 4-acetoxy-1-(α,α-dimethylbenzyl)-3-phenyl-2-pyrrolidinone 6.4 g (20 mmol) of 4-acetoxy-1-(α,α-dimethylbenzyl)-2-oxo-3-phenyl-3-pyrroline prepared by the method of reference Example 14, was dissolved in 100 ml of methanol and subjected to hydrogenation at normal temperature under atmospheric pressure by an addition of 0.4 g of Pd-BaSO$_4$. After completion of the reaction, the catalyst was removed by filtration, and methanol was distilled off. The residue was purified by silica gel column chromatography to obtain 1.0 g (yield: 15%) of the desired compound.

$^1$H-NMR(CDCl$_3$, δ) 1.73(s, 3H), 1.80(s, 3H), 1.87(s, 3H), 3.33(d/d, 1H), 3.70(d/d, 1H), 3.90(d, 1H), 5.43(m, 1H), 7.30(m, 10H)

EXAMPLE 9

Preparation of 1-(α,α-dimethylbenzyl)-3-phenyl-3-pyrrolin-2-one (Compound No. 126)

0.7 g (2 mmol) of 4-acetoxy-1-(α,α-dimethylbenzyl)-3-phenyl-2-pyrrolidinone prepared by the method of Reference Example 15, was dissolved in 30 ml of toluene, and 0.36 g (2.4 mmol) of DBU was added thereto. The mixture was refluxed under heating for five minutes. The reaction solution was cooled, and toluene was added. The toluene solution was thoroughly washed with water and then dried over anhydrous magnesium sulfate. The solvent was distilled off under reduced pressure. The crude product thereby obtained was purified by silica gel column chromatography to obtain 0.4 g (yield: 73%) of the desired compound.

Melting point: 85°–86° C.

$^1$H-NMR(CDCl$_3$, δ) 1.83(s, 6H), 4.00(d, 2H), 7.33(m, 9H), 7.83(m, 2H)

REFERENCE EXAMPLE 16

Preparation of ethyl 3-(α,α-dimethylbenzylamino)propionate 100 g (1 mol) of ethyl acrylate was added to 135.2 g (1 mol) of α,α-dimethylbenzylamine, and the mixture was stirred at 100° C. for 18 hours. The reaction product was subjected to distillation to obtain 180.7 g (yield: 77.8%) of the desired compound.

Boiling point: 110°–125°/0.06 mmHg $^1$H-NMR(CDCl$_3$, δ) 1.23(t, 3H), 1.43(s, 6H), 1.63(br, 1H), 2.50(m, 4H), 4.13(q, 2H), 7.33(m, 5H)

REFERENCE EXAMPLE 17

Preparation of ethyl 3-(N-phenylacetyl-α,α-dimethylbenzylamino)propionate 47.0 g (0.2 mol) of ethyl 3-(α,α-dimethylbenzylamino)propionate prepared by the method of Reference Example 16, was dissolved in 200 ml of acetone, and 30 g (0.22 mol) of potassium carbonate was added thereto. 31.0 g (0.2 mol) phenyl acetic acid chloride was dropwise added thereto at room temperature. After completion of the dropwise addition, the reaction solution was stirred for one day and night, and the reaction solvent was distilled off under reduced pressure. Water was added to the residue, and the mixture was extracted with ethyl acetate, washed with water and then dried over anhydrous magnesium sulfate. The solvent was distilled off under reduced pressure to obtain 63.0 g (yield: 89.1%) of the desired compound.

$^1$H-NMR(CDCl$_3$, δ) 1.27(t, 3H), 1.67(s, 6H), 2.60(m, 2H), 3.47(s, 2H), 3.80(m, 2H), 4.10(q, 2H), 7.17(m, 10)

REFERENCE EXAMPLE 18

Preparation of 1-(α,α-dimethylbenzyl)-3-phenyl-2,4-piperidinedione 12.8 g of sodium metal was added to 500 ml of ethanol to prepare sodium ethylate, and 65.7 g (0.186 mol) of ethyl 3-(N-phenylacetyl-α,α-dimethylbenzylamino)propionate prepared by the method of Reference Example 17 was added thereto. The mixture was refluxed under heating for one hour. The reaction solution was cooled to room temperature, and then ethanol was distilled off under reduced pressure. The residue was poured into ice water and acidified with a 10% hydrochloric acid aqueous solution. Precipitated crystals were collected by filtration. The crude product thereby obtained was recrystallized from ethanol to obtain 29.5 g (yield: 51.6%) of the desired compound.

Melting point: 129°–132° C.

$^1$H-NMR(CDCl$_3$, δ) 1.83(s, 6H), 2.50(t, 2H), 3.37(t, 2H), 4.50(s, 1H), 7.27(m, 10H)

REFERENCE EXAMPLE 19

Preparation of 1-(α,α-dimethylbenzyl)-4-hydroxy-3-phenyl-2-piperidone 4.0 g (0.013 mol) of 1-(α,α-dimethylbenzyl)-2,4-dioxo-3-phenylpiperidine prepared by the method of Reference Example 18, was dissolved in 50 ml of ethanol, and 0.27 g (0.007 mol) of sodium borohydride was added thereto at room temperature. The mixture was stirred at room temperature for 30 minutes, and then ethanol was distilled off under reduced pressure. Water was added to the residue, and precipitated crystals were collected by filtration. The crude product thereby obtained was recrystallized from ethanol to obtain 3.6 g (yield: 90.0%) of the desired compound.

Melting point: 161°–163° C.

$^1$H-NMR(CDCl$_3$, δ) 1.73(s, 6H), 2.07(m, 2H), 3.60(m, 2H), 4.00(m, 2H), 7.20(m, 10H)

REFERENCE EXAMPLE 20

Preparation of 4-acetoxy-1-(α,α-dimethylbenzyl)-3-phenyl-2-piperidone 3.6 g (0.0117 mol) of 4-hydroxy-1-(α,α-dimethylbenzyl)-3-phenyl-2-piperidone prepared by the method of Reference Example 19 and 10 ml of acetic anhydride were dissolved in 20 ml of pyridine, and the mixture was stirred at room temperature for one day and night. After completion of the reaction, the reaction solution was poured into ice water, extracted with ethyl acetate, washed with water and then dried over anhydrous magnesium sulfate. The solvent was distilled off under reduced pressure to obtain 4.1 g (quantitatively) of the desired compound.

Refractive index: 1.5571

$^1$H-NMR(CDCl$_3$, δ) 1.80(s, 6H), 1.93(s, 3H), 2.17(m, 2H), 3.53(m, 2H), 3.80(d, 1H), 5.26(q, 1H), 7.23(m, 10H)

EXAMPLE 10

Preparation of
1-(α,α-dimethylbenzyl)-3-phenyl-1,2,5,6-tetrahydropyridin-2-one (Compound No. 1)

4.2 g (0.012 mol) of 4-acetoxy-1-(α,α-dimethylbenzyl)-3-phenyl-2-piperidone prepared by the method of Reference Example 20, was dissolved in 100 ml of toluene, and 2.7 g (0.018 mol) of DBU was added thereto. The mixture was refluxed under heating for 10 minutes. The reaction solution was cooled to room temperature and washed with water. Then, the solvent was distilled off under reduced pressure. The residual solid was recrystallized from ethanol to obtain 3.0 g (yield: 75.0%) of the desired compound.

Melting point: 119°–120° C.
$^1$H-NMR(CDCl3, δ) 1.80(s, 6H), 2.40(m, 2H), 3.43(t, 2H), 6.60(t, 1H), 7.27(m, 10H)

EXAMPLE 11

Preparation of
1-(3,5-dichloro-4-hydroxy-α,α-dimethylbenzyl)-4-methyl-3-phenyl-3-pyrrolin-2-one (Compound No. 453)

A DMF suspension of 2.2 g (0.05 mol) of sodium hydride (about 60% in oil) was cooled with ice water, and 5.1 g (0.05 mol) of ethyl mercaptan was dropwise added thereto at a temperature not higher than 10° C. under stirring. The reaction mixture was returned to room temperature and left to stand for about 30 minutes. Then, a DMF solution of 15.7 g (0.04 mol) of 1-(3,5-dichloro-4-methoxy-α,α-dimethylbenzyl)-4-methyl-3-phenyl-3-pyrrolin-2-one (Compound No. 143) prepared in Example 2, was added thereto. The solution was heated at about 80° C. and reacted for three hours. After completion of the reaction, the reaction solution was poured into a large amount of ice water, acidified with a 10% hydrochloric acid aqueous solution and then extracted with ethyl acetate. The ethyl acetate layer was dried over anhydrous magnesium sulfate, and then the solvent was distilled off under reduced pressure. The solid thereby obtained was washed with isopropyl ether to obtain 11.0 g (yield: 73.3%) of the desired compound as colorless crystals.

Melting point: 224°–227° C.
$^1$H-NMR(CDCl3, δ) 1.77(s, 6H), 2.15(s, 3H), 3.97 (s, 2H), 7.17(s, 2H), 7.36(m, 6H)

EXAMPLE 12

Preparation of
1-(3,5-dichloro-4-ethoxy-α,α-dimethylbenzyl)-4-methyl-3-phenyl-3-pyrrolin-2-one (Compound No. 438)

0.6 g (0.004 mol) of ethyl iodide and 0.6 g (0.004 mol) of anhydrous calcium carbonate were added to an acetonitrile solution of 1.2 g (0.003 mol) of 1-(3,5-dichloro-4-hydroxy-α,α-dimethylbenzyl)-4-methyl-3-phenyl-3-pyrrolin-2-one prepared in Example 11, and the mixture was refluxed for about 30 minutes under stirring. After completion of the reaction, the reaction mixture was poured into a large amount of water and extracted with ethyl acetate. The ethyl acetate layer was dried over anhydrous magnesium sulfate, and then the solvent was distilled off under reduced pressure. The solid thereby obtained was washed with isopropyl ether to obtain 1.1 g (yield: 91.6%) of the desired compound as colorless crystals.

Melting point: 133°–135° C.
$^1$H-NMR(CDCl3, δ) 1.44(t, 3H), 1.77(s, 6H), 2.16(s, 3H), 4.02(s, 2H), 4.15(q, 2H), 7.25(s, 2H), 7.41(m, 5H)

EXAMPLE 13

Preparation of
1-(3-methylsufonyl-α,α-dimethylbenzyl)-4-methyl-3-phenyl-3-pyrrolin-2-one (Compound No. 383)

A methanol/water (1/1) solution of 2.2 g (0.0065 mol) of 1-(3-methylthio-α,α-dimethylbenzyl)-4-methyl-3-phenyl-3-pyrrolin-2-one (Compound NO. 364) prepared in accordance with the method of Example 2, was cooled to 5° C., and 30 ml of an aqueous solution of 12 g (0.020 mol) of Oxone was dropwise added thereto at a temperature not higher than 5° C. The mixture was stirred at 5° C. for 2 hours and then at room temperature for further 2 hours. 200 ml of ice water and 100 ml of isopropyl ether were added thereto, and the mixture was stirred for 10 minutes. Then, the product was isolated by filtration and washed with diethyl ether to obtain 1.5 g (yield: 62.3%) of the desired compound as white crystals.

Melting point: 162°–164° C.
$^1$H-NMR(CDCl3+DMSO-d6, δ) 1.80(s, 6H) 2.17(s, 3H), 3.08(s, 3H), 4.13(s, 2H), 7.30–8.33(m, 9H)

The herbicidal composition of the present invention comprises a herbicidally effective amount of a cyclic amide compound of the formula I of the present invention and an agricultural adjuvant.

The herbicide of the present invention may be used as it is or may be formulated in various formulations such as wettable powder, a granule, an emulsifiable concentrate or a dust by blending it in an amount of from 0.1 to 95 parts by weight, preferably from 1 to 80 parts by weight, with a carrier, a surfactant, a dispersing agent or an adjuvant which is commonly employed for the formulation of agricultural chemicals, in an amount to make up the total of 100 parts by weight.

As the carrier to be used for the formulation, there may be mentioned a solid carrier such as Zieclite, Zeolite, calcium carbonate, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned.

The proportion of the compound of the present invention in the formulation may vary depending upon the type of the formulation, the application method, the application site, timing, etc. Therefore, it can not generally be defined. However, it is usually from 5 to 60% by weight in a wettable powder, from 5 to 80% by weight in an emulsifiable concentrate, from 1 to 60% by weight in a flowable, from 0.1 to 20% by weight in a granule, from 5 to 40% by weight in a liquid formulation, from 0.1 to 20% by weight in a dust and from 5 to 90% by weight in a dry flowable.

The herbicide is capable of controlling various weeds in a paddy field by irrigated soil treatment before or after the emergence of weed-s or by foliage treatment.

Further, the herbicide of the present invention is capable of controlling various weeds in an agricultural field such as an upland field or an orchard, or in a forest, a lawn or other non-agricultural field by soil treatment before or after the emergence of weeds or by foliage treatment.

For soil treatment, the herbicide of the present invention is applied in a dose of from 0.1 g to 1 kg, preferably from 0.5 to 500 g, more preferably from 1 to 100 g, of the active ingredient per 10 ares. For foliage treatment, it is diluted to a concentration of from 1 to 10,000 ppm for application. Most preferably, it is applied in a dose of from 1 to 10 g of the active ingredient per 10 ares for a paddy field, in a dose of from 5 to 50 g per 10 ares for an orchard or a lawn, and in a dose of from 10 to 100 g for a forest or a non-agricultured field.

Now, Formulation Examples for the herbicidal composition of the present invention will be given. However, it should be understood that the present invention is by no means restricted to these specific Examples. In these Examples, "%" means "% by weight". FORMULATION EXAMPLE 1 (wettable powder)

10 parts of Compound No. 1, 0.5 part of Emulgen 810 (trademark, Kao Corporation), 0.5 part of Demol N (trademark, Kao Corporation), 20 parts of Kunilite 201 (trademark, Kunimine Kogyo K.K.) and 69 parts of Zieclite CA (trademark, Zieclite Company Ltd.) were uniformly mixed and pulverized to obtain a wettable powder.

FORMULATION EXAMPLE 2 wettable powder 10 parts of Compound No. 1, 0.5 part of Emulgen 810 (trademark, Kao Corporation), 0.5 part of Demol N (trademark, Kao Corporation), 20 parts of Kunilite 201 (trademark, Kunimine Kogyo K.K.), 5 parts of Carplex 80 (trademark, Shionogi & Co.) and 69 parts of Ziecklite CA (trademark, Zieclite Company Ltd.) were uniformly mixed and pulverized to obtain a wettable powder.

FORMULATION EXAMPLE 3 emulsifiable concentrate 30 parts of Compound No. 3, 30 parts of xylene, 30 parts of isophorone and 10 parts of surfactant, Solpol 800A (trademark, Toho Kagaku Kogyo K.K.), were mixed and dissolved to obtain an emulsifiable concentrate.

FORMULATION EXAMPLE 4 granule 10 parts of Compound No. 4, 20 parts of talc, 60 parts of bentonite, 5 parts of white carbon, 5 parts of a surfactancet, Solpol 800A and 10 parts of water, were thoroughly kneaded to form a paste, and the paste was extruded through a sieve having a hole diameter of 0.7 mm, dried and cut in a length of from 0.5 to 1 mm to obtain granules.

The compound of the formula I of the present invention exhibits excellent herbicidal activities against annual weeds such as barnyardgrass (*Echinochloa crusgalli*), umbrellaplant (*Cyperus difformis*), monochoria (*Monochoria vaginalis*), toothcup (*Rotala indica*) and false pimpernel (*Lindernia procumbens*), and perennial weeds such as bulrush (*Scirpus hotarui*), slender spikerrush (*Eleocharis acicularis*), waterplantain (*Alisma canaliculatum*) and cyperus (*Cyperus serotinus*) which grow in paddy fields at an extremely low dose over a long period of from the germination to the growing stage of weeds, and at the same time, it is highly safe to paddy rice.

The herbicide of the present invention may be applied directly or to transplanted rice fields. However, it is particularly effective for application to transplanted rice fields.

Further, the herbicide of the present invention has a feature that it exhibits high herbicidal activities against various weeds in upland fields, for example, broad leaf weeds such as smartweed (*Polugonum lapathifolium*), slender amaranth (*Amaranthus viridis*) and common chickweed (*Stellaria media*), perenneal and annual cyperaceous weeds such as purple nutsedge (*Cyperus rotundus*), yellow nutsedge (*Cyperus esculentus*), Kyllinga brevifolia, flatsedge (*Cyperus microiria*) and rice flatsedge (*Cyperus iria*), and gramineous weeds such as barnyardgrass (*Echinochloa crus-galli*), large crabgrass (*Digitaria sanguinalis*), green foxtail (*Setaria viridis*), annual bluegrass (*Poa annua*), Johnsongrass (*Sorghum halepense*) and block grass (*Alopecurus myosuroides*), which are hard to control, by soil treatment or foliage treatment, and at the same time, it is highly safe to crop plants such as soybean (*Glycine max*), cotton (*Gossypium indicum*), sugar beet (*Beta vulgaris*), upland rice (*Oryza sativa*) and wheat (*Triticum aestirum*).

Further, the compound of the present invention is excellent in the residual effect, and exhibits stable effect over a long period of time even in paddy fileds. Further, it can be used to an orchard, a grassland, a lawn, a non-agricultural field or the like.

Now, the effect of the compound of the present invention will be described with reference to Test Examples.

The following abbreviations represent the following test plants:

Eo: *Echinochloa oryzicola*
Cd: umbrellaplant (*Cyperus difformis*)
Mo: Monochoria (*Monochoria vaginalis*)
Sc: bulrush (*Scirpus hotarui*)
Ec: barnyardgrass (*Echinochloa crus-galli*)
Di: large crabgrass (*Digitaria sanguinalis*)
Ci: rice flatsedge (*Cyperus iria*)
Cs: cyperus (*Cyperus serotinus*)
Gl: soybean (*Glycine max*)
Go: cotton (*Gossypium hirsutum*)
Se: green foxtail (*Setaria viridis*)
So: Johnsongrass (*Sorghum halepense*)
Or: rice (*Oryza sativa*)
Tr: wheat (*Triticum aestivum*)
Al: water foxtail (*Alopecurus aequalis*)

TEST EXAMPLE 1

Herbicidal test by soil treatment in a paddy field

In a plastic pot filled with paddy field soil (surface area: 100 cm$^2$), seeds of *Echinochloa oryzicola* (Eo), umbrellaplant (Cd), monochoria (Mo) and bulrush (Sc), were sown, and water was introduced to a depth of 3 cm. Next day, a predetermined amount of a wettable powder prepared in accordance with Formulation Example 1 was diluted with water, and dropwise applied to the water surface at a dose of 400 g of active ingredient per 10 ares. Then, these plants were cultivated in a green house. The evaluation of the herbicidal effect was conducted on the 21st day after the treatment in accordance with the standards as identified in Table 3. The results are shown by the index numbers in Table 4.

TABLE 3

| Index No. | Herbicidal effects and phytotoxicity (degree of growth control) |
|---|---|
| 5 | Herbicidal effect or phytotoxicity: more than 90% control |
| 4 | Herbicidal effect or phytotoxicity: at least 70% and less than 89% |
| 3 | Herbicidal effect or phytotoxicity: at least 50% and less than 69% |
| 2 | Herbicidal effect or phytotoxicity: at least 30% and less than 49% |
| 1 | Herbicidal effect or phytotoxicity: at least 10% and less than 29% |
| 0 | Herbicidal effect or phytotoxicity: at least 0% and less than 9% |

TABLE 4

| Compound No. | Herbicidal effects | | | |
|---|---|---|---|---|
| | Eo | Cd | Ho | Sc |
| 1 | 5 | 5 | 5 | 5 |
| 2 | 5 | 5 | 5 | 5 |
| 3 | 5 | 5 | 5 | 5 |
| 4 | 5 | 5 | 5 | 5 |
| 5 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 11 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 5 | 5 | 5 | 5 |
| 16 | 5 | 5 | 5 | 5 |
| 17 | 5 | 5 | 5 | 5 |
| 18 | 5 | 5 | 5 | 5 |
| 19 | 4 | 5 | 5 | 5 |
| 20 | 5 | 5 | 5 | 5 |
| 21 | 5 | 5 | 5 | 5 |
| 22 | 5 | 5 | 5 | 5 |
| 23 | 5 | 5 | 5 | 5 |
| 24 | 5 | 5 | 5 | 5 |
| 25 | 5 | 5 | 5 | 5 |
| 26 | 5 | 5 | 5 | 5 |
| 27 | 5 | 5 | 5 | 5 |
| 28 | 5 | 5 | 5 | 5 |
| 29 | 5 | 5 | 4 | 5 |
| 30 | 5 | 5 | 5 | 5 |
| 31 | 1 | 5 | 1 | 5 |
| 32 | 1 | 5 | 1 | 5 |
| 33 | 1 | 5 | 1 | 5 |
| 34 | 1 | 5 | 1 | 5 |
| 35 | 5 | 5 | 5 | 5 |
| 36 | 5 | 5 | 5 | 5 |
| 37 | 5 | 5 | 5 | 5 |
| 38 | 5 | 5 | 5 | 5 |
| 39 | 5 | 5 | 5 | 5 |
| 40 | 5 | 5 | 5 | 5 |
| 41 | 5 | 5 | 5 | 5 |
| 42 | 5 | 5 | 5 | 5 |
| 43 | 5 | 5 | 5 | 5 |
| 44 | 5 | 5 | 5 | 5 |
| 45 | 5 | 5 | 5 | 5 |
| 46 | 5 | 5 | 5 | 5 |
| 47 | 5 | 5 | 5 | 5 |
| 48 | 5 | 5 | 5 | 4 |
| 49 | 1 | 5 | 1 | 5 |
| 50 | 3 | 5 | 5 | 5 |
| 51 | 2 | 5 | 1 | 5 |
| 52 | 5 | 5 | 5 | 5 |
| 53 | 5 | 5 | 5 | 5 |
| 54 | 5 | 5 | 5 | 5 |
| 55 | 5 | 5 | 5 | 5 |
| 56 | 5 | 5 | 5 | 5 |
| 57 | 5 | 5 | 5 | 5 |
| 58 | 5 | 5 | 5 | 5 |
| 59 | 5 | 5 | 5 | 5 |
| 60 | 5 | 5 | 5 | 5 |
| 61 | 5 | 5 | 5 | 5 |
| 62 | 5 | 5 | 5 | 5 |
| 63 | 5 | 5 | 5 | 5 |
| 64 | 5 | 5 | 5 | 5 |
| 65 | 5 | 5 | 5 | 5 |
| 66 | 5 | 5 | 4 | 5 |
| 67 | 3 | 5 | 5 | 5 |
| 68 | 5 | 5 | 5 | 5 |
| 69 | 3 | 5 | 1 | 5 |
| 70 | 5 | 5 | 5 | 5 |
| 71 | 5 | 5 | 1 | 5 |
| 72 | 4 | 5 | 5 | 5 |
| 73 | 1 | 5 | 1 | 5 |
| 74 | 1 | 5 | 1 | 5 |
| 75 | 5 | 5 | 5 | 5 |
| 76 | 5 | 5 | 5 | 5 |
| 77 | 5 | 5 | 5 | 5 |
| 78 | 5 | 5 | 5 | 5 |
| 79 | 5 | 5 | 5 | 5 |
| 80 | 5 | 5 | 5 | 5 |
| 81 | 5 | 5 | 5 | 5 |
| 82 | 5 | 5 | 5 | 5 |
| 83 | 5 | 5 | 5 | 5 |
| 84 | 5 | 5 | 5 | 5 |
| 85 | 5 | 5 | 5 | 5 |
| 86 | 5 | 5 | 5 | 5 |
| 87 | 5 | 5 | 5 | 5 |
| 88 | 5 | 5 | 5 | 5 |
| 89 | 5 | 5 | 5 | 5 |
| 90 | 5 | 5 | 5 | 5 |
| 91 | 5 | 5 | 5 | 5 |
| 92 | 5 | 5 | 5 | 5 |
| 93 | 5 | 5 | 5 | 5 |
| 94 | 5 | 5 | 5 | 5 |
| 95 | 5 | 5 | 5 | 5 |
| 96 | 5 | 5 | 5 | 5 |
| 97 | 5 | 5 | 5 | 5 |
| 98 | 5 | 5 | 5 | 5 |
| 99 | 5 | 5 | 5 | 5 |
| 100 | 5 | 5 | 5 | 5 |
| 101 | 5 | 5 | 5 | 5 |
| 102 | 5 | 5 | 5 | 5 |
| 103 | 5 | 5 | 5 | 5 |
| 104 | 5 | 5 | 5 | 5 |
| 105 | 5 | 5 | 5 | 5 |
| 106 | 5 | 5 | 5 | 5 |
| 107 | 5 | 5 | 5 | 5 |
| 108 | 3 | 5 | 5 | 5 |
| 109 | 5 | 5 | 5 | 5 |
| 110 | 5 | 5 | 5 | 5 |
| 111 | 5 | 5 | 5 | 5 |
| 112 | 5 | 5 | 5 | 5 |
| 113 | 5 | 5 | 5 | 5 |
| 114 | 5 | 5 | 5 | 5 |
| 115 | 5 | 5 | 5 | 5 |
| 116 | 5 | 5 | 5 | 5 |
| 117 | 5 | 5 | 5 | 5 |
| 118 | 5 | 5 | 5 | 5 |
| 119 | 5 | 5 | 5 | 5 |
| 120 | 5 | 5 | 5 | 5 |
| 121 | 5 | 5 | 5 | 5 |
| 122 | 5 | 5 | 5 | 5 |
| 123 | 5 | 5 | 5 | 5 |
| 124 | 5 | 5 | 5 | 5 |
| 125 | 5 | 5 | 5 | 5 |
| 126 | 5 | 5 | 5 | 5 |
| 127 | 5 | 5 | 5 | 5 |
| 128 | 5 | 5 | 5 | 5 |
| 129 | 5 | 5 | 5 | 5 |
| 130 | 5 | 5 | 5 | 5 |
| 131 | 5 | 5 | 5 | 5 |
| 132 | 5 | 5 | 5 | 5 |
| 133 | 5 | 5 | 5 | 5 |
| 134 | 5 | 5 | 5 | 5 |
| 135 | 5 | 5 | 5 | 5 |
| 136 | 5 | 5 | 5 | 5 |
| 137 | 5 | 5 | 5 | 5 |
| 138 | 5 | 5 | 5 | 5 |

TABLE 4-continued

| Compound No. | Herbicidal effects | | | |
|---|---|---|---|---|
| | Eo | Cd | Ho | Sc |
| 139 | 5 | 5 | 5 | 5 |
| 140 | 5 | 5 | 5 | 5 |
| 141 | 5 | 5 | 5 | 5 |
| 142 | 5 | 5 | 5 | 5 |
| 143 | 5 | 5 | 5 | 5 |
| 144 | 5 | 5 | 5 | 5 |
| 145 | 5 | 5 | 5 | 5 |
| 146 | 5 | 5 | 5 | 5 |
| 147 | 5 | 5 | 5 | 5 |
| 148 | 5 | 5 | 5 | 5 |
| 149 | 5 | 5 | 5 | 5 |
| 150 | 5 | 5 | 5 | 5 |
| 151 | 5 | 5 | 5 | 5 |
| 152 | 5 | 5 | 5 | 5 |
| 153 | 5 | 5 | 5 | 5 |
| 154 | 5 | 5 | 5 | 5 |
| 155 | 5 | 5 | 5 | 5 |
| 156 | 5 | 5 | 5 | 5 |
| 157 | 5 | 5 | 5 | 5 |
| 158 | 5 | 5 | 5 | 5 |
| 159 | 5 | 5 | 5 | 5 |
| 160 | 5 | 5 | 5 | 5 |
| 161 | 5 | 5 | 5 | 5 |
| 162 | 5 | 5 | 5 | 5 |
| 163 | 5 | 5 | 5 | 5 |
| 164 | 5 | 5 | 5 | 5 |
| 165 | 5 | 5 | 5 | 5 |
| 166 | 5 | 5 | 5 | 5 |

TEST EXAMPLE 2

Herbicidal test by soil treatment in an upland field

In a plastic pot filled with upland soil (surface area: 120 cm$^2$), seeds of barnyardgrass (Ec), large crabgrass (Di) and rice flatsedge (Ci), were sown and covered with soil. A predetermined amount of a wettable powder prepared in accordance with Formulation Example 1 was diluted with water, and uniformly applied to the soil surface at a rate of 100 liters per 10 ares (dose of active ingredient: 400 g/10 ares) by a small spray. Then, these plants were cultivated in a green house. The evaluation of the herbicidal effect was conducted on the 21st day after the treatment in accordance with the standards as identified in Table 3. The results are shown by index numbers in Table 5.

TABLE 5

| Compound No. | Herbicidal effects | | |
|---|---|---|---|
| | Ec | Di | Ci |
| 1 | 4 | 5 | 5 |
| 3 | 5 | 5 | 5 |
| 5 | 5 | 5 | 5 |
| 7 | 5 | 5 | 5 |
| 9 | 5 | 5 | 5 |
| 11 | 5 | 5 | 5 |
| 13 | 3 | 5 | 5 |
| 14 | 5 | 5 | 5 |
| 15 | 5 | 5 | 5 |
| 18 | 5 | 5 | 5 |
| 20 | 5 | 5 | 5 |
| 21 | 5 | 5 | 5 |
| 23 | 5 | 5 | 5 |
| 25 | 5 | 5 | 5 |
| 35 | 5 | 5 | 5 |
| 36 | 5 | 5 | 5 |
| 37 | 5 | 5 | 5 |
| 38 | 5 | 5 | 5 |
| 39 | 5 | 5 | 5 |
| 40 | 5 | 5 | 5 |
| 47 | 4 | 5 | 5 |
| 55 | 5 | 5 | 5 |
| 56 | 5 | 5 | 5 |
| 57 | 5 | 5 | 5 |
| 67 | 5 | 4 | 5 |
| 75 | 5 | 5 | 5 |
| 76 | 5 | 5 | 5 |
| 78 | 5 | 5 | 5 |
| 79 | 5 | 5 | 5 |
| 80 | 5 | 5 | 5 |
| 84 | 5 | 5 | 5 |
| 85 | 5 | 5 | 5 |
| 87 | 5 | 5 | 5 |
| 88 | 5 | 5 | 5 |
| 89 | 5 | 5 | 5 |
| 91 | 5 | 5 | 5 |
| 93 | 5 | 5 | 5 |
| 95 | 5 | 5 | 5 |
| 97 | 5 | 5 | 5 |
| 102 | 5 | 5 | 5 |
| 104 | 5 | 5 | 5 |
| 106 | 5 | 5 | 5 |
| 107 | 5 | 5 | 5 |
| 110 | 4 | 5 | 5 |
| 111 | 5 | 5 | 5 |
| 112 | 5 | 5 | 5 |
| 113 | 5 | 5 | 5 |
| 114 | 5 | 5 | 5 |
| 115 | 5 | 5 | 5 |
| 116 | 5 | 5 | 5 |
| 117 | 5 | 5 | 5 |
| 118 | 5 | 5 | 5 |
| 119 | 5 | 5 | 5 |
| 120 | 5 | 5 | 5 |
| 123 | 5 | 5 | 5 |
| 125 | 5 | 5 | 5 |
| 127 | 5 | 5 | 5 |
| 128 | 5 | 5 | 5 |
| 130 | 5 | 5 | 5 |
| 131 | 5 | 5 | 5 |
| 132 | 5 | 5 | 5 |
| 134 | 5 | 5 | 5 |
| 135 | 5 | 5 | 5 |
| 137 | 5 | 4 | 5 |
| 138 | 5 | 5 | 5 |
| 139 | 5 | 5 | 5 |
| 140 | 5 | 5 | 5 |
| 141 | 5 | 5 | 5 |
| 142 | 5 | 5 | 5 |
| 143 | 5 | 5 | 5 |
| 150 | 5 | 5 | 5 |
| 151 | 5 | 5 | 5 |
| 154 | 5 | 5 | 5 |
| 155 | 5 | 5 | 5 |
| 156 | 5 | 5 | 5 |

TEST EXAMPLE 3

Herbicidal test by foliage treatment in an upland field

In a plastic pot filled with upland soil (surface area: 120 cm$^2$) seeds of barnyardgrass (Ec), large crabgrass (Di) and rice flatsedge (Ci), were sown, and cultivated in a green house until barnyardgrass (Ec) grew to three-leaf stage. At the three-leaf stage of barnyardgrass (Ec), a predetermined amount of a wettable powder prepared in accordance with Formulation Example 1 was diluted with water, and applied to the entire foliage of the plants from the above by a small spray. Then, these plants were cultivated in a green house. The evaluation of the herbicidal effect was conducted on 21st day after the treatment in accordance with the standards as identified in Table 3. The results are shown in Table 6.

TABLE 6

| Compound No. | Herbicidal effects | | |
|---|---|---|---|
| | Ec | Di | Ci |
| 14 | 5 | 5 | 5 |
| 88 | 5 | 5 | 5 |
| 102 | 5 | 5 | 5 |
| 103 | 5 | 5 | 5 |
| 115 | 5 | 5 | 5 |
| 116 | 4 | 5 | 5 |
| 117 | 4 | 4 | 5 |
| 128 | 4 | 4 | 5 |
| 143 | 5 | 4 | 5 |
| 155 | 5 | 5 | 5 |
| 156 | 5 | 5 | 5 |

TEST EXAMPLE 4

Herbicidal effect and phytotoxicity test by soil treatment in a paddy field

A 1/5000 are Wagner pot was filled with paddy soil, and water was introduced and paddled. Then, three tubers of sprouted cyperus (Cs) were buried in the surface soil per a pot, seeds of barnyardgrass (Ec) and bulrush (Sc) were sown, and further, two seedlings of paddy rice (Or) of 2.5-leaf stage were transplanted in a depth of 2 cm. Water was introduced in a depth of 3 cm. Next day, a predetermined amount of a wettable powder prepared in accordance with Formulation Example 1 was diluted with water and dropwise applied to the water surface. Then, these plants were cultivated in a green house. The evaluation of the herbicidal effect and the phytotoxicity were conducted on the 30th day after the treatment in accordance with the standards as identified in table 2. The results are shown by index numbers in Table 7.

TABLE 7

| Compound No. | Dose g/10a | Herbicidal effects | | | Phytotoxicity in paddy rice (Or) |
|---|---|---|---|---|---|
| | | Ec | Sc | Cs | |
| 1 | 50 | 5 | 5 | 5 | 0 |
| 3 | 12.5 | 5 | 5 | 5 | 0 |
| 5 | 6.3 | 5 | 5 | 5 | 0 |
| 9 | 3.1 | 5 | 5 | 5 | 0 |
| 10 | 25 | 5 | 5 | 5 | 0 |
| 11 | 6.3 | 5 | 5 | 5 | 0 |
| 13 | 6.3 | 5 | 5 | 5 | 0 |
| 14 | 12.5 | 5 | 5 | 5 | 0 |
| 15 | 6.3 | 5 | 5 | 5 | 0 |
| 36 | 3.1 | 5 | 5 | 5 | 0 |
| 37 | 6.3 | 5 | 5 | 5 | 0 |
| 39 | 3.1 | 5 | 5 | 5 | 0 |
| 40 | 6.3 | 5 | 5 | 5 | 0 |
| 75 | 6.3 | 5 | 5 | 5 | 0 |
| 76 | 6.3 | 5 | 5 | 5 | 0 |
| 78 | 6.3 | 5 | 5 | 5 | 0 |
| 80 | 6.3 | 5 | 5 | 5 | 0 |
| 84 | 6.3 | 5 | 5 | 5 | 0 |
| 85 | 3.1 | 5 | 5 | 5 | 0 |
| 88 | 3.1 | 5 | 5 | 5 | 0 |
| 89 | 3.1 | 5 | 5 | 5 | 0 |
| 91 | 3.1 | 5 | 5 | 5 | 0 |
| 93 | 6.3 | 5 | 5 | 5 | 0 |
| 102 | 3.1 | 5 | 5 | 5 | 0 |
| 103 | 3.1 | 5 | 5 | 5 | 0 |
| 104 | 3.1 | 5 | 5 | 5 | 0 |
| 110 | 6.3 | 5 | 5 | 5 | 0 |
| 111 | 6.3 | 5 | 5 | 5 | 0 |
| 112 | 6.3 | 5 | 5 | 5 | 0 |
| 113 | 6.3 | 5 | 5 | 5 | 0 |
| 114 | 6.3 | 5 | 5 | 5 | 0 |
| 115 | 6.3 | 5 | 5 | 5 | 0 |
| 116 | 6.3 | 5 | 5 | 5 | 0 |
| 117 | 6.3 | 5 | 5 | 5 | 0 |
| 118 | 6.3 | 5 | 5 | 5 | 0 |
| 119 | 6.3 | 5 | 5 | 5 | 0 |
| 120 | 6.3 | 5 | 5 | 5 | 0 |
| 122 | 6.3 | 5 | 5 | 5 | 0 |
| 125 | 6.3 | 5 | 5 | 5 | 0 |
| 127 | 6.3 | 5 | 5 | 5 | 0 |
| 128 | 6.3 | 5 | 5 | 5 | 0 |
| 130 | 6.3 | 5 | 5 | 5 | 0 |
| 131 | 6.3 | 5 | 5 | 5 | 0 |
| 132 | 6.3 | 5 | 5 | 5 | 0 |
| 134 | 6.3 | 5 | 5 | 5 | 0 |
| 135 | 6.3 | 5 | 5 | 5 | 0 |
| 137 | 6.3 | 5 | 5 | 5 | 0 |
| 138 | 6.3 | 5 | 5 | 5 | 0 |
| 139 | 6.3 | 5 | 5 | 5 | 0 |
| 140 | 6.3 | 5 | 5 | 5 | 0 |
| 141 | 6.3 | 5 | 5 | 5 | 0 |
| 142 | 6.3 | 5 | 5 | 5 | 0 |
| 143 | 6.3 | 5 | 5 | 5 | 0 |

TEST EXAMPLE 5

Selectivity test for crop plants by soil treatment in an upland field

In each plastic pot filled with upland soil (surface area: 600 cm$^2$), seeds of soybean (Gl), cotton (Go), barnyardgrass (Ec), large crabgrass (Di), green foxtail (Se) and Johnsongrass (So), were sown. Water was absorbed from the bottom of the pot. Then, a predetermined amount of a wettable powder prepared in accordance with Formulation Example 1 was diluted with water to bring it to a concentration for application at a rate of 100 liters per 10 ares, and applied to the soil surface by a small spray. After treatment, these plants were again cultivated in a green house. The evaluation of the herbicidal effect and the phytotoxicity were conducted on the 21st day after the treatment in accordance with the standards as identified in Table 3. The results are shown by index numbers in Table 8.

TABLE 8

| Compound No. | Dose g/10a | Phytotoxicity | | Herbicidal effects | | | |
|---|---|---|---|---|---|---|---|
| | | Gl | Go | Ec | Di | Se | So |
| 9 | 25 | 0 | 1 | 5 | 5 | 5 | 5 |
| 14 | 25 | 0 | 0 | 5 | 5 | 5 | 5 |
| 40 | 100 | 0 | 0 | 5 | 5 | 5 | 5 |
| 75 | 6.3 | 0 | 0 | 5 | 5 | 5 | 5 |
| 85 | 25 | 0 | 1 | 5 | 5 | 5 | 5 |
| 86 | 25 | 0 | 1 | 5 | 5 | 5 | 5 |
| 88 | 25 | 1 | 0 | 5 | 5 | 5 | 5 |
| 91 | 25 | 0 | 0 | 5 | 5 | 5 | 4 |
| 97 | 25 | 0 | 0 | 5 | 5 | 5 | 5 |
| 103 | 6.3 | 0 | 0 | 5 | 5 | 5 | 5 |
| 104 | 25 | 0 | 0 | 5 | 5 | 5 | 5 |

TEST EXAMPLE 6 selectivity test for crop plants by soil treatment in an upland field

In each plastic pot filled with upland soil (surface area: 120 cm$^2$), seeds of rice (Or), wheat (Tr), barnyardgrass (Ec), large crabgrass (Di), green foxtail (Se) and block grass (Al), were sown. Water was absorbed from the bottom of the pot. Then, a predetermined amount of a wettable powder prepared in accordance with Formulation Example 1 was diluted with water to bring it to a concentration for application at a rate of 100 liters per 10 ares, and applied on the soil surface by a small spray. After treatment, these plants were again cultivated in a green house. The evaluation of the herbicidal effect and the phytotoxicity were conducted on the 21st day after the treatment in accordance with the standards as identified in Table 3. The results are shown by index numbers in Table 9.

TABLE 9

| Com-<br>pound<br>No. | Dose<br>g/10a | Phyto-<br>toxicity | | Herbicidal effects | | | |
|---|---|---|---|---|---|---|---|
| | | Or | Tr | Ec | Di | Se | Al |
| 14 | 100 | 0 | 0 | 5 | 5 | 5 | 5 |
| 40 | 400 | 0 | 1 | 5 | 5 | 5 | 5 |
| 91 | 25 | 0 | 1 | 4 | 5 | 5 | 4 |
| 97 | 25 | 0 | 0 | 5 | 5 | 5 | 5 |
| 104 | 25 | 1 | 0 | 5 | 5 | 5 | 5 |

We claim:

1. A cyclic amide compound of the formula:

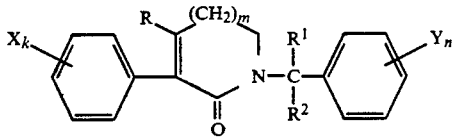

wherein
X is a hydrogen atom, a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a $C_1$-$C_4$ alkylthio group or a nitro group;
Y is a hydrogen atom, a halogen atom, $C_1$-$C_8$ alkyl group, a $C_3$-$C_6$ cycloalkyl group, a $C_2$-$C_8$ alkenyl group, a $C_2$-$C_8$ alkynyl group, a $C_1$-$C_8$ haloalkyl group, a phenyl group, a $C_1$-$C_8$ alkoxy group, a $C_3$-$C_6$ cycloalkoxy group, a $C_3$-$C_6$ cycloalkyl-$C_1$-$C_4$ alkoxy group, a $C_3$-$C_8$ alkenyloxy group, a $C_3$-$C_8$ alkynyloxy group, a benzyloxy group, a phenoxy group, a $C_1$-$C_8$ haloalkoxy group, a $C_1$-$C_4$ alkoxy group, a $C_1$-$C_4$ cyanoalkoxy group, a $C_1$-$C_8$ alkylthio group, a $C_1$-$C_8$ haloalkylthio group, a $C_3$-$C_8$ alkenylthio group, a $C_3$-$C_8$ alkynylthio group, a benzylthio group, a phenylthio group,

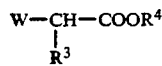

wherein W is an oxygen atom or a sulfur atom, $R^3$ is a hydrogen atom or a $C_1$-$C_4$ alkyl group and $R^4$ is a $C_1$-$C_4$ alkyl group,

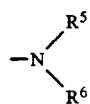

wherein each of $R^5$ and $R^6$ is a hydrogen atom or a $C_1$-$C_4$ alkyl group, a methanesulfonyl group,

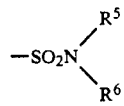

wherein $R^5$ and $R^6$ are as defined above, a $C_1$-$C_4$ alkyl carbonyl group, a $C_1$-$C_4$ alkoxy carbonyl group, a hydroxy carbonyl group, a nitro group, a cyano group or a hydroxyl group;
R is a hydrogen atom or a $C_1$-$C_4$ alkyl group;
each of $R^1$ and $R^2$ is independently a $C_1$-$C_4$ alkyl group, or $R^1$ and $R^2$ together with the adjacent carbon atom form a $C_3$ ring;
m is one;
n is an integer of from 1 to 5; and
k is an integer of 1 or 2.

2. The compound according to claim 1, wherein X is a hydrogen atom, a halogen atom, a $C_1$-$C_4$ alkyl group, a $C_1$-$C_4$ haloalkyl group or a $C_1$-$C_4$ alkoxy group; and Y is a hydrogen atom, a halogen atom, a $C_1$-$C_8$ alkyl group, a $C_1$-$C_8$ haloalkyl group, a $C_1$-$C_8$ alkoxy group, a phenoxy group or a $C_1$-$C_8$ haloalkoxy group.

3. The compound according to claim 1, wherein X is a hydrogen atom or a halogen atom; and Y is a hydrogen atom, a halogen atom, a $C_1$-$C_8$ alkyl group, a $C_1$-$C_8$ haloalkyl group, a $C_1$-$C_8$ alkoxy group or a phenoxy group.

4. The compound according to claim 1, wherein X is a hydrogen atom or a halogen atom; Y is a hydrogen atom, a halogen atom, a $C_1$-$C_8$ alkyl group, a $C_1$-$C_8$ haloalkyl group, a $C_1$-$C_8$ alkoxy group or a phenoxy group; R is a methyl group; and each of $R^1$ and $R^2$ is a methyl group.

5. The compound according to claim 1, wherein R is a hydrogen atom, a methyl group or an ethyl group; and each of $R^1$ and $R^2$ is a methyl group.

6. The compound according to claim 2, wherein R is a hydrogen atom, a methyl group or an ethyl group; and each of $R^1$ and $R^2$ is a methyl group.

7. The compound according to claim 3, wherein R is a hydrogen atom, a methyl group or an ethyl group; and each of $R^1$ and $R^2$ is a methyl group.

8. The compound according to claim 1, wherein when n is an integer of 1, 2 or 3, Y is a hydrogen atom or a halogen atom.

9. The compound according to claim 2, wherein when n is an integer of 1, 2, or 3, Y is a hydrogen atom or a halogen atom.

10. The compound according to claim 3, wherein when n is an integer of 1, 2, or 3, Y is a hydrogen atom or a halogen atom.

11. The compound according to claim 4, wherein when n is an integer of 1, 2, or 3, Y is a hydrogen atom or a halogen atom.

12. The compound according to claim 1, wherein when n is 3, two or three Y are halogen atoms.

13. The compound according to claim 2, wherein when n is 3, two or three Y are halogen atoms.

14. The compound according to claim 3, wherein when n is 3, two or three Y are halogen atoms.

15. The compound according to claim 4, wherein when n is 3, two or three Y are halogen atoms.

16. A herbicidal composition comprising a herbicidally effective amount of a cyclic amide compound of the formula I as defined in claim 1, and an agricultural adjuvant.

17. A method for killing weeds which comprises applying a herbicidally effective amount of a cyclic amide compound of the formula I as defined in claim 1, to a locus to be protected.

18. The method of claim 17, wherein said locus to be protected contains crop plants.

* * * * *